US006638713B2

(12) United States Patent
Makings et al.

(10) Patent No.: US 6,638,713 B2
(45) Date of Patent: Oct. 28, 2003

(54) OPTICAL MOLECULAR SENSORS FOR CYTOCHROME P450 ACTIVITY

(75) Inventors: Lewis R. Makings, Encinitas, CA (US); Gregor Zlokarnik, La Jolla, CA (US)

(73) Assignee: Aurora Biosciences Corporation, San Diego, CA (US)

(*) Notice: Subject to any disclaimer, the term of this patent is extended or adjusted under 35 U.S.C. 154(b) by 0 days.

(21) Appl. No.: 09/995,961

(22) Filed: Nov. 27, 2001

(65) Prior Publication Data

US 2003/0027238 A1 Feb. 6, 2003

Related U.S. Application Data

(63) Continuation of application No. 09/301,525, filed on Apr. 28, 1999, now Pat. No. 6,420,130.
(60) Provisional application No. 60/112,252, filed on Dec. 14, 1998.

(51) Int. Cl.[7] .............................. C12Q 1/00; C12Q 1/68; C07D 279/18; C07D 401/00; C07D 277/78
(52) U.S. Cl. .................. 435/4; 435/7.6; 435/4; 435/25; 435/41; 435/6; 544/40; 546/18; 548/158; 549/26
(58) Field of Search ................ 435/25, 4, 7.6, 435/41, 6; 544/40; 546/18; 548/158; 549/26

(56) References Cited

U.S. PATENT DOCUMENTS

| 4,200,577 A | 4/1980 | Buckle et al. ............. 424/281 |
| 4,810,636 A | 3/1989 | Corey ......................... 435/14 |

(List continued on next page.)

FOREIGN PATENT DOCUMENTS

| EP | 0 032 036 | 7/1981 |
| EP | 0110682 | 6/1984 |

(List continued on next page.)

OTHER PUBLICATIONS

Aitio, Analyt. Biochem., 85:488–91(1978).
Berman et al., J. of Medicinal Chemistry, 40:827–829 (1997).
Buckle et al., Chemical Abstracts, vol. 93:186172 (1980).

(List continued on next page.)

*Primary Examiner*—Jezia Riley
(74) *Attorney, Agent, or Firm*—Knobbe, Martens, Olson & Bear, LLP

(57) ABSTRACT

The invention provides methods of using a compound as an optical probe or sensor of the activity of at least one cytochrome P450 enzyme, and methods of using the compound to screen candidate drugs, and kits for performing these methods. The optical probe of the invention is a compound having the generic structure Y-L-Q, wherein Y is selected from the group consisting of Q as herein defined, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl and substituted heteroaryl; L is selected from the group of $(-OCR^2H)_p-$, wherein for each p, all $R^2$ are separately selected from the group consisting of a hydrogen atom, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl, substituted heteroaryl, and p is a positive integer no greater than twelve; and Q is a chemical moiety that gives rise to optical properties in its hydroxy or hyrdoxylate, phenol or phenoxide form that are different from the optical properties that arise from its ether form. Most preferably, p is one, $R^2$ is hydrogen, and Q is the ether form of a phenoxide fluorophore.

10 Claims, 7 Drawing Sheets

U.S. PATENT DOCUMENTS

| | | | |
|---|---|---|---|
| 5,110,725 A | 5/1992 | Marrone et al. | 435/11 |
| 5,208,332 A | 5/1993 | Marrone et al. | 514/102 |
| 5,304,645 A | 4/1994 | Klein et al. | 544/102 |
| 5,741,657 A | 4/1998 | Tsien et al. | 435/18 |
| 6,143,492 A | 11/2000 | Makings et al. | 435/4 |

FOREIGN PATENT DOCUMENTS

| | | |
|---|---|---|
| EP | 0373104 | 8/1989 |
| EP | 0363793 | 4/1990 |
| GB | 2211500 | 5/1989 |
| WO | WO 87/03541 | 6/1987 |
| WO | WO 97/39064 | 10/1997 |
| WO | WO 99/58710 | 11/1999 |
| WO | WO 00/04008 | 1/2000 |

OTHER PUBLICATIONS

Burke et al., Biochem J. 212: 15–14 (1983).

Burke et al., Biochemical Pharmacology, 34: 3337–33345 (1985).

Buters, Jeroen, *A Highly Sensitive Tool for the Assay of CYP450 Enzyme*; Biochemical Pharmacology, vol. 46:9, 1577–84 (1993).

Crespi et al., Advances in Pharmacology, 43: 171–188 (1997).

Crespi et al., Analytical Biochemistry, 248: 188–190 (1997).

DeLuca et al., Biochemical Pharmacology, 37: 1731–1739 (1988).

Donato et al., Analytical Biochemistry, 213: 29–33 (1993).

Greenlee et al., J. Pharmacology and Experimental Therapeutics, 205: 596–605 (1978).

Gotoh, J. of Biological Chemistry, 267: 83–90 (1992).

Haasch, Mary, *Use of 7–Alkoxyphenoxazones, 7–Alkoxycoumarins A. 7–Alkoxyquinolines As Flourescent Substrates*; Biochemical Pharmacology, vol. 47:5, 893–903 (1994).

Kennedy et al., Analytical Biochemistry, 222: 217–223 (1994).

Klotz et al., Analytical Biochemistry, 140: 138–145 (1984).

Koller et al., "Syntheses and Spectral Properties of Long-wave Absorbing and Fluorescing Substrates for the Direct and Continuous Kinetic Assay of Carboxylesterases, Phosphatases, and Sulfatases," *Monashefte für Chemie* 116, 65–75 (1985).

Krafft, Grant, *Photoactivable Fluorophores 3*; Journal of the American Chemical Society., vol. 110, 301–303 (1988).

Kronbach et al., Analytical Biochemistry, 162: 24–32 (1987).

Mace, et al., *Development of CYP450–expressing human bronchial epithelial cell lines for in vitro pharmacotoxicologic applications*; In Vitro Toxicology, vol. 10, 85–92 (1997).

Maeda et al., "Studies on the Preparation of Bioactive Lignans by Oxidative Coupling Reaction. VI.[1] Oxidation of Methyl (E)–3–(4,5–Dihydroxy–2–methoxyphenyl)–2–butenoate and Lipid Peroxidation–Inhibitory Effects of the Produced Caffeoquinone," *Chem. Pharm. Bull.*, 43(9) 1588–1591 (1995).

Maeda et al., "Studies on the Preparation of Bioactive Lignans by Oxidative Coupling Reaction. II.[1] Oxidative Coupling Reaction of Methyl (E)–3–(4,5–Dihydroxy–2–methoxyphenyl)propenoate and Lipid Peroxidation Inhibitory Effects of the Produced Lignans," *Chem. Pharm. Bull.*, 42(12) 2506–2513 (1994).

Maeda et al., "Studies on the Preparation of Bioactive Lignans by Oxidative Coupling Reaction. III.[1] Synthesis of Polyphenolic Benzofuran and Coumestan Derivatives by Oxidative Coupling Reaction of Methyl (E)–3–(4–Hydroxy–2–methoxyphenyl)propenoate and Their Inhibitory Effect on Lipid Peroxidation," *Chem. Pharm. Bull.* 42(12) 2536–2545 (1994).

Maeda et al., Chemical Abstracts, vol. 124:116791 (1995).

Maeda et al., Chemical Abstracts, vol. 122:265145 (1995).

Marrone et al., Endocrinology, 128: 2654–2656 (1991).

Mayer, R.T., *7–Alkoxyquinolines: New Fluorescent Substrates for Cytochrome P450 Monooxygenases*, Biochemical Pharmacology, vol. 40:7, 1645–55 (1990).

Mayer et al., Biochemical Pharmacology, 38: 1364–1368 (1989).

Miller, Analytical Biochemistry, 133: 46–57 (1983).

Murray, Clinical Pharmacokinetic Concepts, 23: 133–146 (1992).

Murray et al., Pharmacological Reviews, 42: 85–101 (1990).

Omata, Yoshiaki, *Conformational Change of CYP–450*, Biochimica et Biophysica Acta vol. 870, 392–400 (1986).

Ono et al., Xenobiotica, 26: 681–693 (1996).

Parkinson, "An Overview of Current CYP–450 Technology," Toxicologic Pathology, 24: 45–57 (1996).

Peck et al., J. American Medical Ass., 269: 1550–1552 (1993).

Schalk et al., Biochemistry 36: 15253–15261 (1997).

Sherman et al., "Fluorescence of Substituted 7–Hydroxycoumarins," *Analytical Chemistry* 40(4) 803–805 (1968).

Shultz et al., "Synthesis of Bis(semiquinone)s and Their Electrochemical and Electron Paramagnetic Resonance Spectra Characterization," *J. Org. Chem*, 63, 9462–9469 (1998).

Shultz et al., Chemical Abstracts, vol. 130:139089 1998.

Simpson et al., J. Org. Chem. 56: 5391–5396 (1991).

Smith et al., Research Focus, 2: 406–414 (1997).

Smith et al., Research Focus, 2: 479–486 (1997).

Smith et al., Biochemical Pharmacology, 44: 2089–2098 (1992).

Thummel et al., Annul. Rev. Pharmacol. Toxicol., 38: 389–430 (1998).

Wheelock, "The Fluorescence of Some Coumarins," *J. Amer. Chem. Soc.*, vol. 81, pp. 1348–1352 (1958).

White, Ian N.H., *A Continuous Fluorometric Assay for CYP–450*, Analytical Biochemistry, vol. 172–2, 304–310 (1988).

White et al., Biochem, J., 247: 23–28 (1987).

Wrigton et al., J. Pharmacokinetics and Biopharmaceutics, 25: 461–473 (1996).

OPTICAL MOLECULAR SENSORS FOR CYTOCHROME P450 ACTIVITY

PRIORITY CLAIM

This application claims priority from, and is a continuation of U.S. application Ser. No. 09/301,525, filed Apr. 28, 1999 now U.S. Pat. No. 6,420,130; which application claims priority from U.S. Provisional Application Ser. No. 60/112, 252, filed Dec. 14, 1998.

BACKGROUND OF THE INVENTION

1. Field of the Invention

This invention relates to novel chemical compounds, useful as optical indicators of cytochrome P450 activity, and especially to fluorogenic indicators of cytochrome P450 activity. More specifically, the invention relates to ether-containing compounds of the generic structure Y-L-Q, and to methods for assaying substrates and inhibitors of cytochrome P450 enzymes using these compounds in traditional assay formats, as well as in high and ultra high throughput screening formats.

2. Description of the Related Art

The cytochrome P450 enzyme (CYP450) family comprises oxidase enzymes involved in the xenobiotic metabolism of hydrophobic drugs, carcinogens, and other potentially toxic compounds and metabolites circulating in blood. It is known that the liver is the major organ for xenobiotic metabolism, containing high levels of the most important CYP450 mixed-function oxygenases. There are numerous human P450 enzyme sub-families, often termed "isozymes" or "isoforms." Those of the CYP 3A4, CYP 2D6, CYP 2C, CYP 2A1 and CYP 2E1 subfamilies are known to be important in drug metabolism. See, e.g., Murray, M., 23 Clin. Pharmacokinetics 132–46 (1992). Of these isoforms, CYP 3A4 is by far the major isoform in liver and the small intestines, comprising 30% and 70% respectively of the total CYP450 protein in those tissues. Based primarily on in vitro studies, it has been estimated that the metabolism of 40% to 50% of all drugs used in humans involve CYP 3A4 catalyzed oxidations. See Thummel, K. E. & Wilkinson, G. R., *In Vitro and In Vivo Drug Interactions Involving Human CYP 3A*, 38 Ann. Rev. Pharmacol. Toxicol., 389–430 (1998).

Efficient metabolism of a candidate drug by a CYP450 enzyme may lead to poor pharmacokinetic properties, while drug candidates that act as potent inhibitors of a CYP450 enzyme can cause undesirable drug—drug interactions when administered with another drug that interacts with the same CYP450. See, e.g., Peck, C. C. et al., *Understanding Consequences of Concurrent Therapies*, 269 JAMA 1550–52 (1993). Accordingly, early, reliable indication that a candidate drug interacts with (i.e., is a substrate or inhibitor of) a CYP450 may greatly shorten the discovery cycle of pharmaceutical research and development, and thus may reduce the time required to market the candidate drug. Consequently, such earlier-available, reliable CYP450 pharmokinetic information may result in greatly reduced drug development costs and/or increased profits from earlier market entrance. Furthermore, such earlier-available, reliable CYP450 pharmokinetic information may allow a candidate drug to reach the public sooner, at lower costs than otherwise feasible. Accordingly, extensive pharmacokinetic studies of drug interactions in humans have recently become an integral part of the pharmaceutical drug development and safety assessment process. See, e.g., Parkinson, A., 24 Toxicological Pathology 45–57 (1996). Methodologies are therefore desired that will allow for (1) the more rapid acquisition of information about drug candidate interactions with CYP450 enzymes, earlier in the drug discovery process than presently feasible, and hence will allow for (2) the earlier elimination of unsuitable compounds and chemical series from further development efforts.

The need for information regarding drug candidate/ CYP450 interactions has created a concurrent need for assays sensitive enough to test, in a cost-effective manner, vast arrays of compounds for interactions with the major human CYP450 enzymes involved in drug metabolism. Certain known techniques, including (1) CYP450 inhibition assays in which the metabolism of known CYP450 metabolite in the presence of the test compound, followed by quenching of the enzyme reaction and analysis of the extent of metabolism, (2) CYP450 metabolism of radioactively labeled test compound analogues, and (3) in vivo "cassette" dosing of animals (usually rats, dogs, or monkeys), see Berman, J. et al., Simultaneous Pharmacokinetic Screening of a Mixture of Compounds in the Dog using API LC/MS/ MS Analysis for Increased Throughput, 40 J. Medicinal Chemistry, 827–29 (1997), are not amenable to adaptation to miniaturization, or to the other requirements of high or ultra high throughput screening.

However, optical assays employing, for example, chromophores or luminescent phenols, and especially fluorescence-based assays are amendable to adaptation to miniaturization and high or ultra high throughput screening. Particularly, fluorescence-based assays have been used in pharmacokinetic studies of drug interactions in humans, more particularly in assays involving human hepatocyte cultures, where the number of available cells is severely limited. See Donato, M. T. et al, 213 Anal. Biochem. 29–33 (1993).

Specifically, fluorogenic cytochrome P450 substrates have been commercially available for a number of years from, for example, Molecular Probes, Inc. (Eugene Oreg.), SIGMA (St. Louis, Mo.), and more recently, GENTEST Corp. (Woburn, Mass.). Generally, these known fluorogenic CYP450 substrates are ether derivatives of well-known phenoxide type fluorophores, including: 7-hydroxycoumarin, fluorescein, and resorufin. Thus, generally, the CYP450 enzymes will catalyze a dealkylation reaction and convert the relatively non-fluorescent ether substrate into a relatively more highly-fluorescent phenoxide-containing product.

However, even the most recently developed fluorogenic CYP450 substrates either have relatively poor kinetics, or the enzymatic products do not have the desired physical and optical properties to allow reduction of the amount of enzyme needed to levels that would make large scale screening affordable and feasible. More specifically, these fluorogenic CYP450 substrates exhibit relatively poor turnover rates, poor aqueous solubility, low extinction coefficients and quantum yields, and/or weak fluorescence of the resultant phenolic dye. Furthermore, certain of these fluorogenic CYP450 substrates are excited in the ultraviolet, as opposed to visible, spectrum and therefore their signals are often masked by background stemming from the unreacted test compound. Finally, most of these fluorogenic CYP450 substrates are not specific for the CYP450 isozyme they are meant to detect, and therefore cannot be used for measurement in human liver microsomal preparations, a preferred analytical method that avoids potential artifacts caused by the alternative method of using an insect cell microsomal preparation. See Palamanda J. R. et al., *Validation of a rapid microtiter plate assay to conduct cytochrome P450 2D6 enzyme inhibition studies*, 3 Drug Discovery Today, 466–470 (1998). For these and other reasons, there exists an unfulfilled need for optical, and especially fluorogenic, CYP450 substrates that exhibit CYP450 isozyme-specificity, improved kinetics, and yield enzymatic products having improved physical and optical properties for use in the screening of CYP450/drug candidate interactions, especially for use in high or ultra high throughput screening, and as part of the drug discovery process.

SUMMARY OF THE INVENTION

The invention provides a compound, useful as an optical probe, modulator or sensor of the activity of at least one cytochrome P450 enzyme. The optical probe of the invention is a compound having the generic structure Y-L-Q, wherein Y is selected from the group consisting of Q as herein defined (such that the probe has the general structure Q-L'-Q), and saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl and substituted heteroaryl; L is selected from the group of (—$OCR^2H)_p$—, (—O(substituted ortho-phenyl)$CR^2H)_p$—, (—O(substituted meta-phenyl)$CR^2H)_p$—, and (—O(substituted para-phenyl)$CR^2H)_p$—, and L' is selected from the group of —($CR^4H$)(—$OCR^2H)_p$—, —($CR^4H$)(—O(substituted ortho-phenyl)$CR^2H)_p$—, —($CR^4H$)(—O(substituted meta-phenyl)$CR^2H)_p$—, and —($CR^4H$)(—O(substituted para-phenyl)$CR^2H)_p$—, wherein for each p, each $R^2$ is separately selected from the group consisting of a hydrogen atom, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl, substituted heteroaryl and p is a positive integer no greater than twelve; and Q is a chemical moiety that gives rise to optical properties in its hydroxy or hyrdoxylate, phenol or phenoxide form that are different from the optical properties that arise from its ether form. Most preferably, p is one, $R^2$ is hydrogen, and Q is the ether form of a phenoxide fluorophore.

The invention also provides methods for using the optical sensor compounds of the invention to determine whether a candidate drug, or class of candidate drugs, is a CYP450 substrate and/or whether the candidate drug, or class of candidate drugs, is a CYP450 inhibitor, and related methods for selecting a candidate drug, and for formulating and administering that drug, having determined that the drug will not be metabolized by at least one CYP450 enzyme and/or that the drug will not act as an inhibitor of at least one CYP450 enzyme, and, thus, having determined that the drug will not, respectively, be too efficiently metabolized by a CYP 450 enzyme and/or elicit an unfavorable drug—drug interaction. Methods of selecting the candidate drug of the present invention may be by conventional methods or may be part of high or ultra high throughput screening of libraries of drug candidates.

BRIEF DESCRIPTION OF THE DRAWINGS

The accompanying drawings, which are incorporated in and form part of the specification, merely illustrate embodiments of the present invention. Together with the remainder of the specification, they are meant to serve to explain the principles of the invention to those of skill in the art. In the drawings.

DETAILED DESCRIPTION OF THE PREFERRED EMBODIMENT

Figure 1:
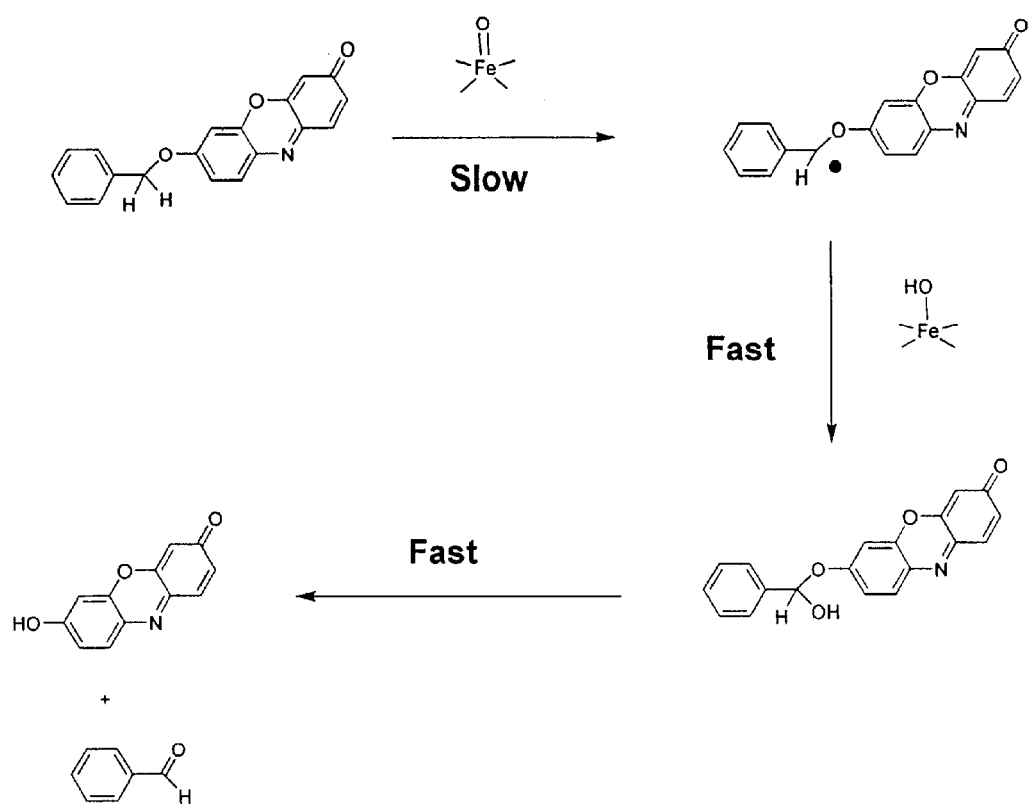
FIG. 1 illustrates Reaction Scheme 1, which shows a reaction mechanism for the CYP450 dealkylation of a currently-available fluorogenic CYP450 substrate, phenoxazone.

Members of the cytochrome P450 enzyme (CYP) family primarily catalyze epoxidation and hydroxylation reactions. Hydroxylation of a fluorogenic phenoxide ether liberates the free phenoxide which is readily detected by virtue of its fluorescence. The mechanisms of CYP450-catalyzed dealkylation reactions have been extensively studied and can be envisioned to proceed via the route depicted in Reaction Scheme 1, as illustrated in FIG. 1. See Groves, J. T. et al., *Models and Mechanisms of Cytochrome P450 Action,* in "Cytochrome P450: Structure, Mechanism, Biochemistry," Plenum Press, 3–48, 1997. Experimental evidence suggests that the rate-limiting step in the reaction is the hydrogen abstraction reaction illustrated in the first step of Reaction Scheme 1, as illustrated in FIG. 1. Accordingly, a fluorogenic substrate with a faster turnover rate, especially with regard to the rate-limiting step, may be desired to achieve the needs inherent in the art. A class of such substrates, the optical sensor compounds of the present invention, is provided, wherein the abstraction of any of the additional hydrogen atoms still generates a free compound in its hydroxy or hydroxylate, usually phenoxide, form which exhibits superior optical properties than the compound in its ether form.

The present invention provides, in a preferred embodiment, for the "insertion" of an oxymethyl linker between the fluorophore and the reactive ether moiety attached to the leaving group. Such an "insertion" is accomplished, according to, for example, the synthetics methods of EXAMPLES 1 through 7, which are preferred methods of preparing the optical CYP450 sensors of the present invention.

Generally, as will be appreciated upon review of EXAMPLES 1 through 7 by persons of skill in the art, compounds of the present invention may be synthesized according to the following reaction scheme:

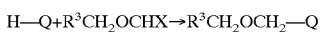

wherein X is a suitable leaving group, for example a halogen atom, a tosyl group, a mesyl group, a triflate group, and wherein the reaction is carried out in the presence of, preferably, $DMF/K_2CO_3$, diisopropylethylamine/DMF at temperatures at or slightly above the freezing point of water; wherein Q is a compound which exhibits superior optical properties in its hydroxy or hydroxylate, typically but not exclusively phenoxide, form than it does as in its ether form, and is preferably a fluorophore or a chromophore, and is most preferably a fluorophore selected from the group consisting of 7-hydroxycoumarin, resorufin, and the known phenoxide fluorophores; and $R^3$ is selected from the group consisting of Q as herein defined, $R^1$ of the known fluorogenic cytochrome P450 substrates, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl and substituted heteroaryl.

Furthermore, and more generally descriptive of compounds of the present invention, one of the methyl protons of the linker may be replaced by a distinct chemical group, $R^2$, wherein $R^2$ is selected from the group consisting of saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl and substituted heteroaryl groups. Furthermore, multiple, linked oxymethyl, or more generally, multiple $OCR^2H$, groups may form the linker of the CYP450 sensor of the invention. In a multimeric linker the $R^2$ groups are selected independently from each other. For example, a linker denoted $(CR^2H)_p$ with p=3 has following structure: —$(OCR^{2(1)}H)$—$(OCR^{2(2)}H)$—$(OCR^{2(3)}H)$—, in which $R^{2(1)}$ and $R^{2(2)}$ and $R^{2(3)}$ are independently selected from the group consisting of a hydrogen atom, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl and substituted heteroaryl.

The present invention therefore provides compounds, useful as optical probes for quantifying the activity of at least one cytochrome P450 enzyme; said compound having the generic structure Y-L-Q wherein:

Y is selected from the group consisting of (i) Q as herein defined, so long as L is L' as herein defined, and (ii) the group consisting of saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl and substituted heteroaryl.

L is selected from the group of $(-OCR^2H)_p-$, (—O(substituted ortho-phenyl)$CR^2H)_p-$, (—O(substituted meta-phenyl)$CR^2H)_p-$, and (—O(substituted para-phenyl)$CR^2H)_p-$, wherein for each p, each $R^2$ is separately selected from the group consisting of a hydrogen atom, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl and substituted heteroaryl, and p is a positive integer no greater than twelve. When Y is selected from Q as herein defined, L is L', wherein L' is selected from the group of $-(CR^4H)(-OCR^2H)_p-$, $-(CR^4H)(-O$ (substituted ortho-phenyl)$CR^2H)_p-$, $-(CR^4H)(-O$ (substituted meta-phenyl)$CR^2H)_p-$, and $-(CR^4H)(-O$ (substituted para-phenyl)$CR^2H)_p-$, wherein each $R^2$ and $R^4$ is separately selected from the group consisting of a hydrogen atom, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl and substituted heteroaryl, and p is a positive integer no greater than twelve.

Use of the structures Q-L'-Q of the CYP450 sensor of the invention has the advantage of yielding two, instead of one, optical Q moieties in the hydroxy or hydroxylate form upon interaction of the optical sensor of the invention with at least one CYP450 enzyme.

The terms substituted ortho-phenyl, substituted meta-phenyl, and substituted para-phenyl refer to a phenyl that is part of the linker connecting Y with Q in which ortho, meta, and para refer to positions of the carbons in the phenyl ring that serve as the attachment for Y and Q. Ortho substituted refers to attachment of Y and Q via adjacent carbons in the phenyl ring, meta substituted refers to attachment of Y and Q by carbons spaced by one carbon on the phenyl ring, and para substitution refers to the attachment of Y and Q on the phenyl ring by carbons that are spaced by two carbons on the phenyl ring. When used in defining additional substitution of the phenyl ring in the oxyphenylmethyl linker the term substituted refers to the substitution of the remaining carbons not involved in attachment of Y and Q on the phenyl ring The term "substituted" means any substitution of a hydrogen atom with a functional group. Functional groups are selected from the group consisting of a halogen atom, $C_1$–$C_{20}$ alkyl, substituted $C_1$–$C_{20}$ alkyl, perhalogenated alkyl, cyloalkyl, substituted cycloalkyl, aryl, substituted aryl, benzyl, heteroaryl, substituted heteroaryl, cyano, nitro, —$SR_S$, —$OR_O$, —$NR_{n1}R_{n2}$, —$N^+R_{n1}R_{n2}R_{n3}$, —N=N—$R_{n1}$, —$P^+R_{n1}R_{n2}R_{n3}$, —$COR_C$, —C(=$NOR_O$)$R_C$, —$CSR_C$, —$OCOR_C$, —$OCONR_{n1}R_{n2}$, —$OCO_2R_C$, —$CONR_{n1}R_{n2}$, —C(=N)$NR_{n1}R_{n2}$, —$CO_2R_O$, —$SO_2NR_{n1}R_{n2}$, —$SO_3R_O$, —$SO_2R_O$, —PO($OR_O$)$_2$, —$NR_{n1}CSNR_{n2}R_{n3}$, —$NR_{n1}$C(=N)$NR_{n2}R_{n3}$, —$NR_{n1}CONR_{n2}R_{n3}$, —$NR_{n1}COR_C$ and —$NR_{n1}$S(=O)$_2R_S$. Substituents $R_{n1}$, $R_{n2}$, $R_{n3}$, $R_O$ and $R_S$ are each separately selected from the group consisting of a hydrogen atom, $C_1$–$C_{20}$ alkyl, substituted $C_1$–$C_{20}$ alkyl, cyloalkyl, substituted cycloalkyl, aryl, substituted aryl, benzyl, heteroaryl, substituted heteroaryl and may constitute parts of an aliphatic or aromatic heterocycle. $R_C$ is selected from the group consisting of a hydrogen atom, $C_1$–$C_{20}$ alkyl, substituted $C_1$–$C_{20}$ alkyl, perhalogenated alkyl, cyloalkyl, substituted cycloalkyl, aryl, substituted aryl, benzyl, heteroaryl, substituted heteroaryl and cyano. Also, when used in the context of defining Y and $R^2$, the term "substituted" means any substitution of a hydrogen with a functional group as defined herein so long as hetero-atom substitution does not occur at the α-carbon.

The term "quencher" refers to a chromophoric molecule or part of a compound, which is capable of reducing the emission from a fluorescent donor when attached to the donor. Quenching may occur by any of several mechanisms including fluorescence resonance energy transfer, photoinduced electron transfer, paramagnetic enhancement of inter-system crossing, Dexter exchange coupling, and exciton coupling such as the formation of dark complexes.

The term "acceptor" refers to a quencher that operates via energy transfer. Acceptors may re-emit the transferred energy as fluorescence and are "acceptor fluorescent moieties". Examples of acceptors include coumarins and related fluorophores, xanthenes such as fluoresceins, rhodols, and rhodamines, resorufins, cyanines, difluoroboradiazaindacenes, and phthalocyanines. Other chemical classes of acceptors generally do not re-emit the transferred energy as light. Examples include indigos, benzoquinones, anthraquinones, azo compounds, nitro compounds, indoanilines, and di- and triphenylmethanes.

Q is attached to L through an ether linkage via the oxygen indicated by the arrow, and has a structure selected from the group consisting of the following structures:

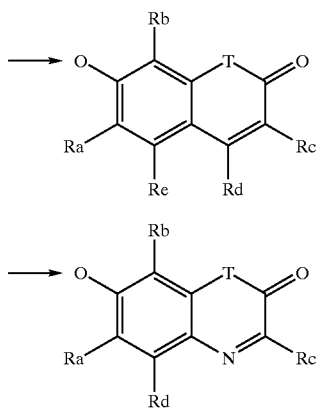

I

II

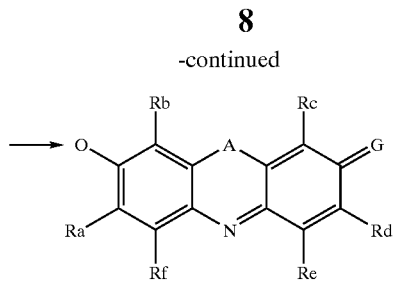

III

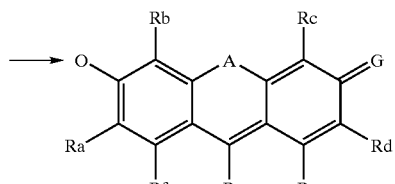

IV

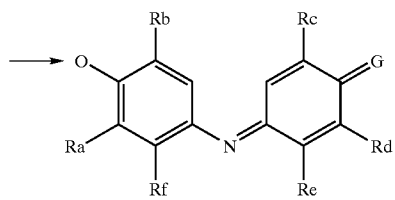

V

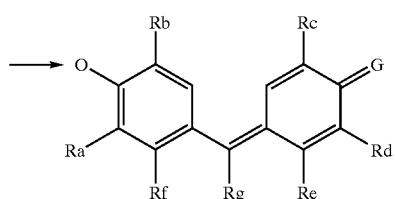

VI

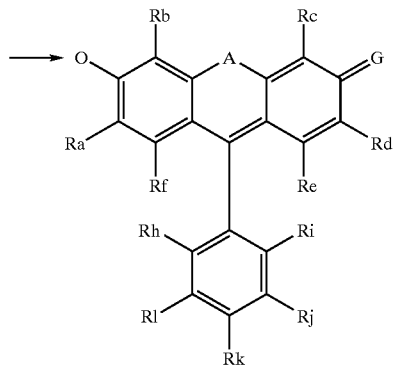

VII

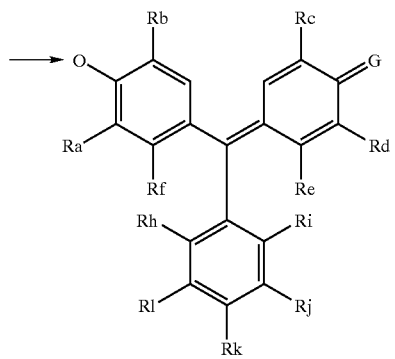

VIII

-continued
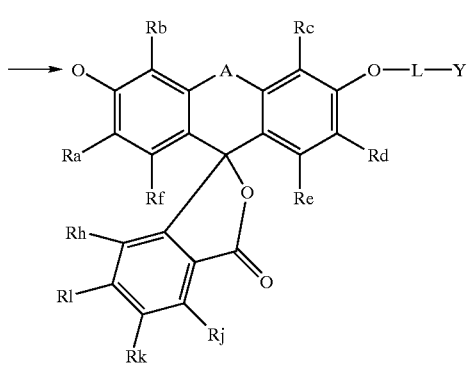 IX
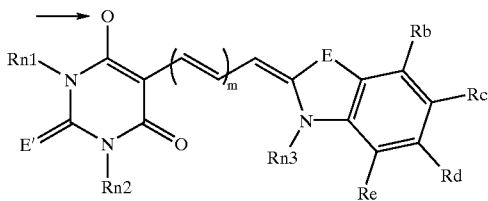 XIV
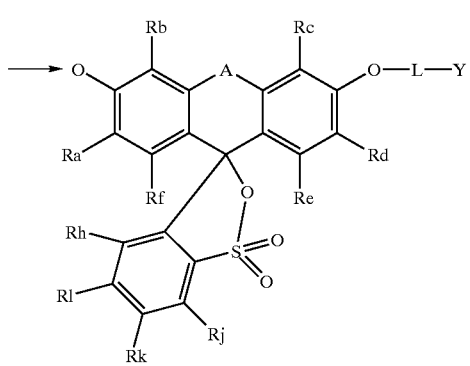 X
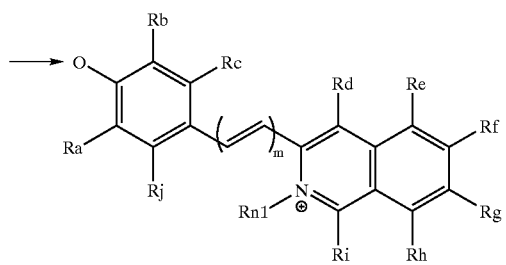 XV
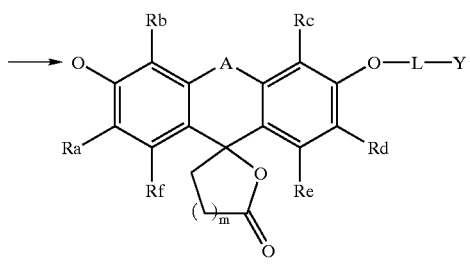 XI
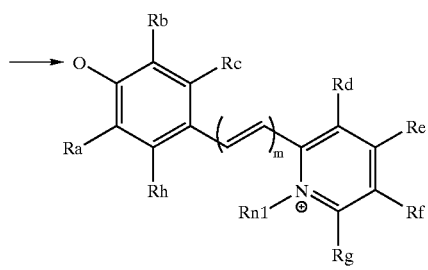 XVI
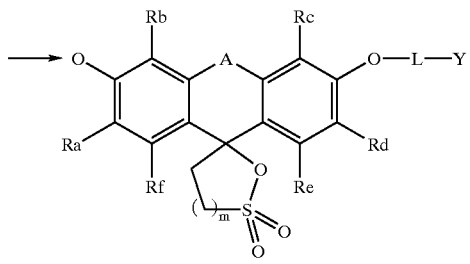 XII
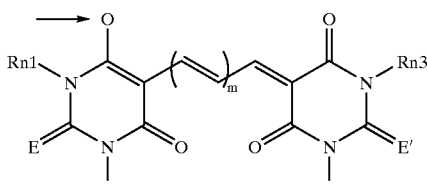 XVII
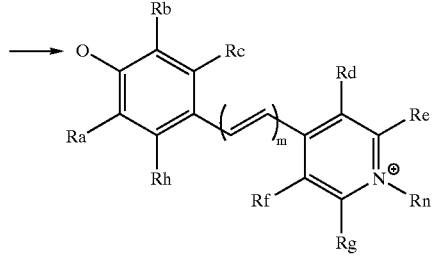 XVIII
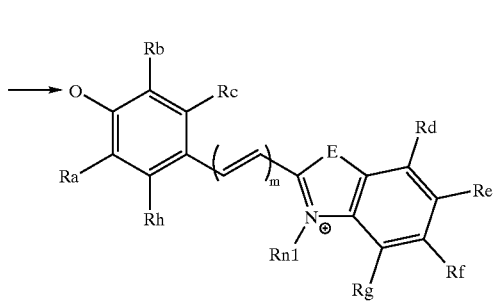 XIII
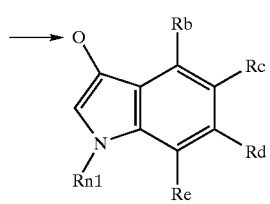 XIX

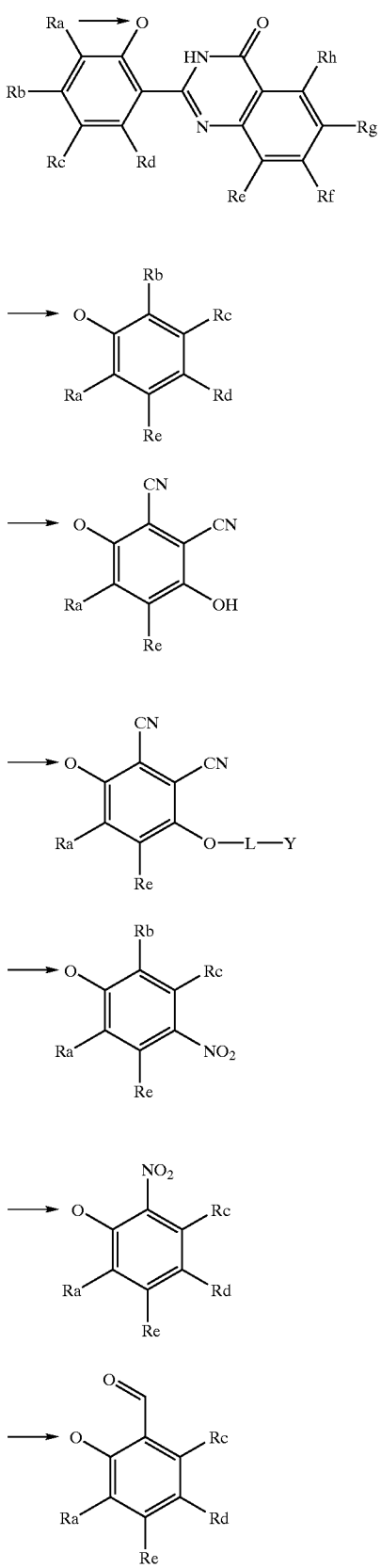

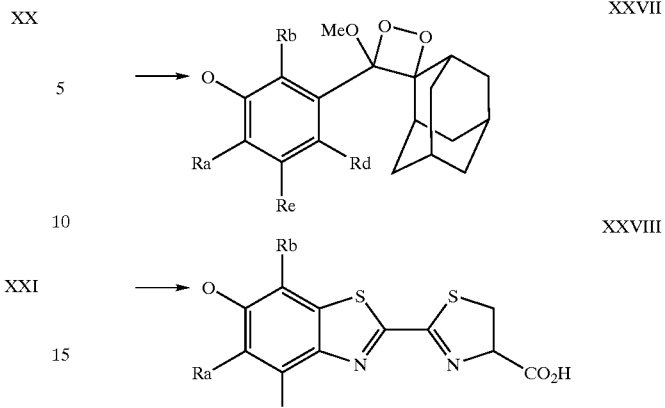

wherein:

m is a positive integer no greater than five;

$R_a$, $R_b$, $R_c$, $R_d$, $R_e$, $R_f$ $R_g$, $R_h$, $R_i$, $R_j$, $R_k$, and $R_l$ are each separately selected from the group consisting of a hydrogen atom, a halogen atom, $C_1$–$C_{20}$ alkyl, substituted $C_1$–$C_{20}$ alkyl, perhalogenated alkyl, cyloalkyl, substituted cycloalkyl, aryl, substituted aryl, benzyl, heteroaryl, substituted heteroaryl, cyano, nitro, azido, —$SR_S$, —$OR_O$, —$NR_{n1}R_{n2}$, —$N^+R_{n1}R_{n2}R_{n3}$, —N=N—$R_{n1}$, —$P^+R_{n1}R_{n2}R_{n3}$, —$COR_C$, —C(=$NOR_O$)$R_C$, —$CSR_C$, —$OCOR_C$, —$OCONR_{n1}R_{n2}$, —$OCO_2R_C$, —$CONR_{n1}R_{n2}$, —C(=N)$NR_{n1}R_{n2}$, —$CO_2R_O$, —$SO_2NR_{n1}R_{n2}$, —$SO_3R_O$, —$SO_2R_O$, —PO(O$R_O$)$_2$, —$NR_{n1}CSNR_{n2}R_{n3}$, —$NR_{n1}$C(=N)$NR_{n2}R_{n3}$, —$NR_{n1}CONR_{n2}R_{n3}$, —$NR_{n1}COR_C$ and —$NR_{n1}S(=O)_2R_S$;

$R_{n1}$, $R_{n2}$, $R_{n3}$, $R_O$ and $R_S$ are each separately selected from the group consisting of a hydrogen atom, $C_1$–$C_{20}$ alkyl, substituted $C_1$–$C_{20}$ alkyl, cyloalkyl, substituted cycloalkyl, aryl, substituted aryl, benzyl, heteroaryl, substituted heteroaryl and may constitute parts of an aliphatic or aromatic heterocycle;

$R_C$ is selected from the group consisting of a hydrogen atom, $C_1$–$C_{20}$ alkyl, substituted $C_1$–$C_{20}$ alkyl, perhalogenated alkyl, cyloalkyl, substituted cycloalkyl, aryl, substituted aryl, benzyl, heteroaryl, substituted heteroaryl, cyano and may constitute parts of an aliphatic or aromatic homo- or heterocycle;

A is selected from the group consisting of an oxygen atom, a sulfur atom, SO, $SO_2$, C($CH_3$)$_2$ and C($CF_3$)$_2$;

E and E' are separately selected from the group consisting of an oxygen atom, a sulfur atom and $NR_{n1}$;

G is selected from the group consisting of an oxygen atom, a sulfur atom, and $NR_{n1}R_{n2}$, wherein if G is selected from $NR_{n1}R_{n2}$, G and $R_c$, as well as G and $R_d$, may constitute parts of a heterocycle; and T is selected from the group consisting of an oxygen atom and $NR_{n1}$.

As will be appreciated by reference to the presently presented examples of the optical CYP450 sensors of the present invention, the preferred optical sensors of the present invention are fluorogenic CYP450 sensors wherein Q is the ether form of a phenoxide fluorophore. Furthermore, the forgoing examples of Q are meant to highlight the point that Q may be any chemical structure, so long as Q is a chemical means for generating an altered optical signal via cleavage of a C—O bond. Those of skill in the art will recognize variations to the structures of Q herein described to achieve this function. Furthermore, the function of generating an altered optical signal via cleavage of a C—O bond may be achieved by releasing a dye upon cleavage of a C—O bond or, more preferably, by releasing a fluorescent dye upon cleavage of a C—O bond, and even more preferably, by releasing a phenolic fluorescent dye upon cleavage of a C—O bond. Preferably, the altered optical signal is an enhanced optical signal.

In the case where Q is an ether form of a fluorophore, Y may act as a quencher. In this case, CYP450 activity is detected by an increase in fluorescence from Q, which is due to the loss of quenching of its fluorescence by Y. If fluorescence quenching by Y occurs via fluorescence resonance energy transfer, then Y is referred to as an acceptor. In the case where Q is an ether form of a fluorophore and Y acts as a quencher, attachment of Y-L to Q can by substitution of any hydrogen on the fluorophore by Y-L-O-, the O denoting an oxygen atom. In this case Q can be any fluorophore, the ether form of which being formed by substitution of one ore more fluorophore hydrogen atoms by Y-L-O-. See U.S. Pat. No. 5,741,657 to Tsien and Zlokarnik (issued Apr. 21, 1998), which is incorporated by reference herein.

In the optical CYP450 sensors of the present invention, Y is preferably selected from $C_1$–$C_8$, alkyl, $C_1$–$C_8$ alkenyl, substituted $C_2$–$C_8$ alkyl, substituted $C_2$–$C_8$ alkenyl, alkoxyalkyl, aryl, substituted aryl, tertiary and quarternary aminoalkyl and guanidinium groups. Among the aryls and substituted aryls, benzyl, and substituted benzyl groups are most preferred. Most preferably, Y is selected from methyl, ethyl, propyl, isopropyl, butyl, isobutyl, tert-butyl, pentyl, octyl and benzyl.

Preferably, L is selected from the group consisting of —(OCR$^2$H)$_p$— and —(O-para-phenyl-CR$^2$H)$_p$— wherein R$^2$ is a hydrogen atom or methyl, and p equals either one or two. Most preferably R$^2$ is a hydrogen atom and p equals one.

Preferably, Q is a fluorophore. More preferably, Q is selected from the group consisting of 7-hydroxycoumarin, resorufin, fluorescein and other phenoxide fluorophores. Nevertheless Q may be a chromophore, so long as it exhibits optical properties in its hydroxy or hydroxylate form, e.g., after interaction with an active CYP450 enzyme, that differ from its ether form, e.g., in its unreacted state. Most generally, Q is a chemical moiety that exhibits optical properties in its free hydroxy or its hydroxylate, usually phenoxide, form that are different from the optical properties that it exhibits in its ether form. Suitable structures of Q, as used herein, may also be found in U.S. Pat. No. 5,741,657 which is incorporated by reference herein.

The optical CYP450 sensor compounds of the present invention may be used to determine CYP450 activities by a variety of optical signals, including for example, in the context of (a) the CYP450-catalyzed formation of chromogenic or fluorgenic or luminescent phenols, (b) the CYP450-catalyzed formation of chromogenic or fluorgenic precipitates, (c) the CYP450-catalyzed light generation from conversion of a phenolic dioxetane substrate, (d) the CYP450-catalyzed liberation of a salicilate or other phenolic ligand detectable by heavy metal chelate formation to give a colored, fluorescent, phosphorescent or electrochemiluminescent product, and (e) the CYP450-catalyzed liberation of a sensitizer for light generation by peroxide/luminol, and (f) the CYP450-catalyzed liberation of a substrate suitable for secondary enzyme detection (e.g., the liberation of a luciferin, which may be detected by a luciferase).

As used herein, the terms "halogen" and "halogen atom" refer to any one of the radio-stable atoms of column 17 of the Periodic Table of the Elements, i.e., fluorine, chlorine, bromine, or iodine, with fluorine and chlorine being most preferred.

As used herein, the term "alkyl" means any unbranched, branched or cyclic, saturated hydrocarbon, with $C_1$–$C_8$ unbranched, saturated, unsubstituted hydrocarbons being preferred, and with methyl, ethyl, propyl, isopropyl, butyl, isobutyl, tert-butyl, n-pentyl and n-octyl being most preferred.

The term "substituted alkyl" means any unbranched, branched or cyclic, substituted saturated hydrocarbon substituted with one or more functional groups. Functional groups are selected from the group consisting of a halogen atom, $C_1$–$C_{20}$ alkyl, substituted $C_1$–$C_{20}$ alkyl, perhalogenated alkyl, cyloalkyl, substituted cycloalkyl, aryl, substituted aryl, benzyl, heteroaryl, substituted heteroaryl, cyano, nitro, —SR$_S$, —OR$_O$, —NR$_{n1}$R$_{n2}$, —N$^+$R$_{n1}$R$_{n2}$R$_{n3}$, —P$^+$R$_{n1}$R$_{n2}$R$_{n3}$, —COR$_C$, —C(=NOR$_O$)R$_C$, —CSR$_C$, —OCOR$_C$, —OCONR$_{n1}$R$_{n2}$, —OCO$_2$R$_C$, —CONR$_{n1}$R$_{n2}$, —C(=N)NR$_{n1}$R$_{n2}$, —CO$_2$R$_O$, —SO$_2$NR$_{n1}$R$_{n2}$, —SO$_3$R$_O$, —SO$_2$R$_O$, —PO(OR$_O$)$_2$, —NR$_{n1}$CSNR$_{n2}$R$_{n3}$, —NR$_{n1}$C(=N)NR$_{n2}$R$_{n3}$, —NR$_{n1}$CONR$_{n2}$R$_{n3}$, —NR$_{n1}$COR$_C$ and —NR$_{n1}$S(=O)$_2$R$_S$. Substituents R$_{n1}$, R$_{n2}$, R$_{n3}$, R$_O$ and R$_S$ are each separately selected from the group consisting of a hydrogen atom, $C_1$–$C_{20}$ alkyl, substituted $C_1$–$C_{20}$ alkyl, cyloalkyl, substituted cycloalkyl, aryl, substituted aryl, benzyl, heteroaryl, substituted heteroaryl and may constitute parts of an aliphatic or aromatic heterocycle. R$_C$ is selected from the group consisting of a hydrogen atom, $C_1$–$C_{20}$ alkyl, substituted $C_1$–$C_{20}$ alkyl, perhalogenated alkyl, cyloalkyl, substituted cycloalkyl, aryl, substituted aryl, benzyl, heteroaryl, substituted heteroaryl and cyano. When used in the context of defining Y and R$^2$, the term "substituted alkyl" means any unbranched or branched, substituted saturated hydrocarbon, so long as hetero-atom substitution does not occur at the α-carbon.

The term "alkenyl" means any unbranched, branched or cyclic, substituted or unsubstituted, unsaturated hydrocarbon, with $C_1$–$C_8$ unbranched, mono-unsaturated and di-unsaturated being preferred. The term "substituted alkenyl" means any unbranched or branched, substituted unsaturated hydrocarbon substituted with one or more functional groups. Functional groups are selected from the group consisting of a halogen atom, $C_1$–$C_{20}$ alkyl, substituted $C_1$–$C_{20}$ alkyl, perhalogenated alkyl, cyloalkyl, substituted cycloalkyl, aryl, substituted aryl, benzyl, heteroaryl, substituted heteroaryl, cyano, nitro, —SR$_S$, —OR$_O$, —NR$_{n1}$R$_{n2}$, —N$^+$R$_{n1}$R$_{n2}$R$_{n3}$, —P$^+$R$_{n1}$R$_{n2}$R$_{n3}$, —COR$_C$, —C(=NOR$_O$)R$_C$, —CSR$_C$, —OCOR$_C$, —OCONR$_{n1}$R$_{n2}$, —OCO$_2$R$_C$, —CONR$_{n1}$R$_{n2}$, —C(=N)NR$_{n1}$R$_{n2}$, —CO$_2$R$_O$, —SO$_2$NR$_{n1}$R$_{n2}$, —SO$_2$NR$_{n1}$R$_{n2}$, —SO$_3$R$_O$, —SO$_3$R$_O$, —SO$_2$R$_O$, —PO(OR$_O$)$_2$, —NR$_{n1}$CSNR$_{n2}$R$_{n3}$, —NR$_{n1}$C(=N)NR$_{n2}$R$_{n3}$, —NR$_{n1}$CONR$_{n2}$R$_{n3}$, —NR$_{n1}$COR$_C$ and —NR$_{n1}$S(=O)$_2$R$_S$. Substituents R$_{n1}$, R$_{n2}$, R$_{n3}$, R$_O$ and R$_S$ are each separately selected from the group consisting of a hydrogen atom, $C_1$–$C_{20}$ alkyl, substituted $C_1$–$C_{20}$ alkyl, cyloalkyl, substituted cycloalkyl, aryl, substituted aryl, benzyl, heteroaryl, substituted heteroaryl and may constitute parts of an aliphatic or aromatic heterocycle. R$_C$ is selected from the group consisting of a hydrogen atom, $C_1$–$C_{20}$ alkyl, substituted $C_1$–$C_{20}$ alkyl, perhalogenated alkyl, cyloalkyl, substituted cycloalkyl, aryl, substituted aryl, benzyl, heteroaryl, substituted heteroaryl, cyano and may constitute parts of an aliphatic or aromatic homo- or heterocycle. When used in the context of defining Y and R$^2$, the term "substituted alkenyl" means any unbranched or branched, substituted unsaturated hydrocarbon, so long as neither the carbon—carbon double bond, nor heteroatom substitution occurs at the α-carbon.

The terms "aryl," "substituted aryl," "heteroaryl," and "substituted heteroaryl" refer to aromatic hydrocarbon rings, preferably having five or six atoms comprising the ring. The term "substituted aryl" includes mono and poly-substituted aryls, substituted with functional groups selected from the group of a halogen atom, $C_1$–$C_{20}$ alkyl, substituted $C_1$–$C_{20}$ alkyl, perhalogenated alkyl, cyloalkyl, substituted cycloalkyl, aryl, substituted aryl, benzyl, heteroaryl, substituted heteroaryl, cyano, nitro, azido, —$SR_S$, —$OR_O$, —$NR_{n1}R_{n2}$, —$N^+R_{n1}R_{n2}R_{n3}$, —$N=N-R_{n1}$, —$P^+R_{n1}R_{n2}R_{n3}$, —$COR_C$, —$C(=NOR_O)R_C$, —$CSR_C$, —$OCOR_C$, —$OCONR_{n1}R_{n2}$, —$OCO_2R_C$, —$CONR_{n1}R_{n2}$, —$C(=N)NR_{n1}R_{n2}$, —$CO_2R_O$, —$SO_2NR_{n1}R_{n2}$, —$SO_3R_O$, —$SO_2R_O$, —$PO(OR_O)_2$, —$NR_{n1}CSNR_{n2}R_{n3}$, —$NR_{n1}C(=N)NR_{n2}R_{n3}$, —$NR_{n1}CONR_{n2}R_{n3}$, —$NR_{n1}COR_C$ and —$NR_{n1}S(=O)_2R_S$. Substituents $R_{n1}$, $R_{n2}$, $R_{n3}$, $R_O$ and $R_S$ are each separately selected from the group consisting of a hydrogen atom, $C_1$–$C_{20}$ alkyl, substituted $C_1$–$C_{20}$ alkyl, cyloalkyl, substituted cycloalkyl, aryl, substituted aryl, benzyl, heteroaryl, substituted heteroaryl and may constitute parts of an aliphatic or aromatic heterocycle. $R_C$ is selected from the group consisting of a hydrogen atom, $C_1$–$C_{20}$ alkyl, substituted $C_1$–$C_{20}$ alkyl, perhalogenated alkyl, cyloalkyl, substituted cycloalkyl, aryl, substituted aryl, benzyl, heteroaryl, substituted heteroaryl, cyano, and may constitute parts of an aliphatic or aromatic homo- or heterocycle. "Heteroaryl" and "substituted heteroaryl," refer to aromatic hydrocarbon rings in which at least one heteroatom, e.g., oxygen, sulfur, or nitrogen atom, is in the ring along with at least one carbon atom.

The terms substituted ortho-phenyl, substituted meta-phenyl, and substituted para-phenyl refer to a phenyl that is part of the linker connecting Y with Q in which ortho, meta and para refer to position of the carbons in the phenyl ring that serve as the attachment for Y and Q. Ortho substituted refers to attachment of Y and Q via adjacent carbons in the phenyl ring, meta substituted refers to attachment of Y and Q by carbons spaced by one carbon on the phenyl ring and para substitution refers to the attachment of Y and Q on the phenyl ring by carbons that are spaced by two carbons on the phenyl ring. When used in defining additional substitution of the phenyl ring in the oxyphenylmethyl linker, the term "substituted" refers to the substitution of hydrogens on the remaining carbons not involved in attachment of Y and Q on the phenyl ring. The term "substituted phenyl" includes mono and poly-substituted phenyls, substituted with functional groups. Functional groups are selected from the group consisting of a halogen atom, $C_1$–$C_{20}$ alkyl, substituted $C_1$–$C_{20}$ alkyl, perhalogenated alkyl, cyloalkyl, substituted cycloalkyl, aryl, substituted aryl, benzyl, heteroaryl, substituted heteroaryl, cyano, azido, nitro, —$SR_S$, —$OR_O$, —$NR_{n1}R_{n2}$, —$N^+R_{n1}R_{n2}R_{n3}$, —$P^+R_{n1}R_{n2}R_{n3}$, —$COR_C$, —$C(=NOR_O)R_C$, —$CSR_C$, —$OCOR_C$, —$OCONR_{n1}R_{n2}$, —$OCO_2R_C$, —$CONR_{n1}R_{n2}$, —$C(=N)NR_{n1}R_{n2}$, —$CO_2R_O$, —$SO_2NR_{n1}R_{n2}$, —$SO_3R_O$, —$SO_2R_O$, —$PO(OR_O)_2$, —$NR_{n1}CSNR_{n2}R_{n3}$, —$NR_{n1}C(=N)NR_{n2}R_{n3}$, —$NR_{n1}CONR_{n2}R_{n3}$, —$NR_{n1}COR_C$ and —$NR_{n1}S(=O)_2R_S$. Substituents $R_{n1}$, $R_{n2}$, $R_{n3}$, $R_O$ and $R_S$ are each separately selected from the group consisting of a hydrogen atom, $C_1$–$C_{20}$ alkyl, substituted $C_1$–$C_{20}$ alkyl, cyloalkyl, substituted cycloalkyl, aryl, substituted aryl, benzyl, heteroaryl, substituted heteroaryl and may constitute parts of an aliphatic or aromatic heterocycle. $R_C$ is selected from the group consisting of a hydrogen atom, $C_1$–$C_{20}$ alkyl, substituted $C_1$–$C_{20}$ alkyl, perhalogenated alkyl, cyloalkyl, substituted cycloalkyl, aryl, substituted aryl, benzyl, heteroaryl, substituted heteroaryl, cyano, and may constitute parts of an aliphatic or aromatic homo- or heterocycle.

The term "fluorogenic CYP450 substrate" generally refers to any compound that, upon interacting with a CYP450 enzyme, exhibits superior fluorescence properties than the compound exhibited prior to interacting with the CYP450 enzyme. As used herein, the terms "optical probe" and "optical sensor," are synonymous, each referring to a compound that can be used to assay an activity that catalyzes the conversion of the ether form of the compound to the hydroxy or hydroxylate, usually phenoxide, form of the compound by virtue of the fact that each contains a chemical moiety that exhibits optical properties in its hydroxy or hydroxylate, usually its phenoxide, form, that are distinct from, and preferably superior to, the optical properties that the chemical moiety exhibits as an ether. The terms "optical CYP450 probe," and "optical CYP450 sensor" are synonymous; each is a broader term than "fluorogenic CYP450 substrate;" each refers to a compound that may be used to assay the presence and, especially where a CYP450 inhibitor may be present, the activity of at least one CYP450 enzyme by virtue of the fact that each contains a chemical moiety that exhibits optical properties in its hydroxy or hydroxylate, usually its phenoxide, form, that are distinct from, and preferably superior to, the optical properties that the chemical moiety exhibits as an ether. By virtue of the fact that at least one CYP450 enzyme will catalyze the conversion of the ether form to the hydroxy or hydroxylate, usually phenoxide, form, these optical probes or sensors may be used to assay the presence and activity of at least one CYP450 enzyme.

The term "reagent compound" refers to the compounds of the invention, as herein described, especially the compounds of general structure Y-L-Q. The term "candidate compound" is a term broader than the terms "candidate drug" and "candidate modulator," as those term are used herein, and refers to any compound, of whatever origin, suitable for being screened for its activity as a substrate or inhibitor of a CYP450 enzyme according to the methods of the present invention.

Within the present invention, long wavelength fluorescence dyes are preferred over dyes that are excited in the V, but all fluorescence dyes, as well as dyes that are excited in the UV or IR, are useful as Q in the optical sensor compounds and the methods of the invention.

Many screening compound libraries often contain fluorescent compounds. Typically the fluorescent compounds in libraries have absorbances in the UV or short wavelength visible portion of the spectrum. Thus, for many fluorescent assays, longer wavelength reporter molecules usually result in assays that have lower background and less interference. In addition, compounds of the present invention preferable have improved solubility in both water and acetonitrile compared to the most closely related CYP450 substrates currently available. Aqueous solubility is important, as 1–20 μM substrate concentrations are needed to lead to a strong fluorescence signal in the assay. Good solubility in acetonitrile (1–10 mM) allows the delivery of the hydrophobic substrate molecules into the aqueous assay medium in small volumes. Acetonitrile is a preferred solvent, as it does not inhibit CYP450 at concentrations up to 2%. Other solvents, such as DMSO and ethanol, typically used to deliver hydrophobic molecules into the aqueous assay medium do inhibit the activity of most CYP450 enzymes at lower concentrations and are therefore not preferred substrate delivery. However, as is known, CYP450 and related compounds do tolerate DMSO at concentrations up to 0.5%, permitting delivery of test compounds to the assay medium in this solvent.

With reference to the following structure, it has been demonstrated that the introduction of an oxymethyl spacer ($R^2$=H) between the moiety $R^1$ and the phenolic dye of currently-available fluorogenic CYP450 sensors tends to increase the efficiency ($k_{cat}/K_m$) of turnover by many CYP450 enzymes and related compounds. $R^1$ of currently available fluorogenic CYP450 sensors are alkyl or substituted methyl, with the Substituent being an aryl group or a steroid, see U.S. Pat. No. 5,110,725. An optical CYP450 probe of the present invention, shown in the following structure, illustrates this "insertion" to provide the optical CYP450 sensor compounds of the present invention.

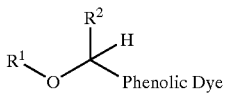

This improved turnover, and improved optical properties, have been demonstrated for a variety of structurally distinct substrates. Furthermore, solubilities of substrates of the invention in acetonitrile, as well as water, are excellent, overcoming one of the above-mentioned limitations of the currently available fluorogenic CYP450 substrates. Accordingly, the above structure illustrates optical CYP450 sensor compounds of the present invention, wherein $R^1$ is a structure as herein defined for Y. Thus, $R^1$ in the above structure of CYP450 sensor compounds of the present invention is selected from a group consisting of all Y as herein defined. However, the groups corresponding to $R^1$ that are found on presently, commercially-available phenol CYP450 ether substrates, are but a subset of Y as herein defined; compounds having the linker of the present invention and employing groups corresponding to $R^1$ that are found in presently, commercially-available phenol CYP450 ether substrates-compounds lacking the linker of the present invention-exhibit improved physical and optical properties with respect to presently, commercially-available phenol CYP450 ether substrates.

$R^2$ in the above structure of CYP450 sensor compounds of the present invention is selected from the group consisting of a hydrogen atom, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl and substituted heteroaryl groups, as those terms are herein defined.

Furthermore, it has been demonstrated that the introduction of an oxyphenylmethyl spacer ($R^2$=H) between the moiety $R^1$ and the phenolic dye of currently-available fluorogenic CYP450 sensors also tends to increase the efficiency ($k_{cat}/K_m$) of turnover by CYP450 enzymes and related compounds.

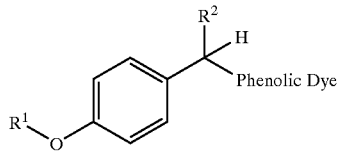

Accordingly, the above structure illustrates oxyphenylmethyl containing optical CYP450 sensor compounds of the present invention, wherein $R^1$ is a structure as herein defined for Y. Thus, $R^1$ in the above structure of CYP450 sensor compounds of the present invention is selected from a group consisting of all Y as herein defined. However, the groups corresponding to $R^1$ that are found on presently, commercially-available phenol CYP450 ether substrates, are but a subset of Y as herein defined; compounds having the linker of the present invention and employing groups corresponding to $R^1$ that are found in presently, commercially-available phenol CYP450 ether substrates-compounds lacking the linker of the present invention-exhibit improved physical and optical properties with respect to presently, commercially-available phenol CYP450 ether substrates.

$R^2$ in the above structure of CYP450 sensor compounds of the present invention is selected from the group consisting of a hydrogen atom, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl and substituted heteroaryl, as those terms are herein defined.

Figure 2:
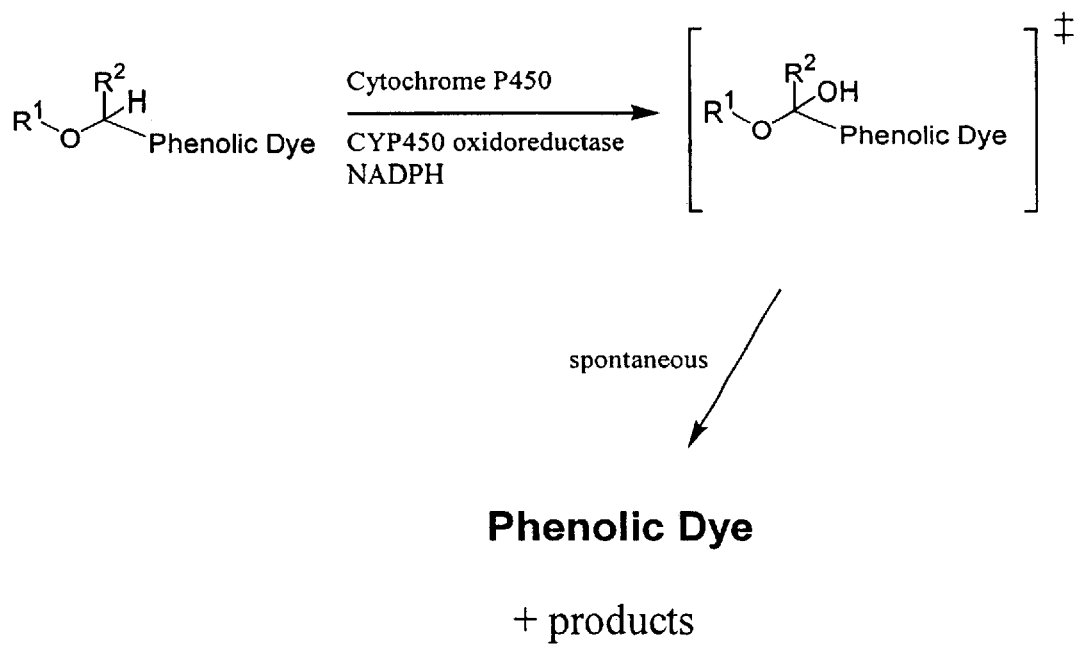
FIG. 2 illustrates Reaction Scheme 2, which shows a generic structure of the optical CYP450 substrate/sensor of the present invention, and the CYP450-catalyzed hydroxylation reaction.
Figure 3:
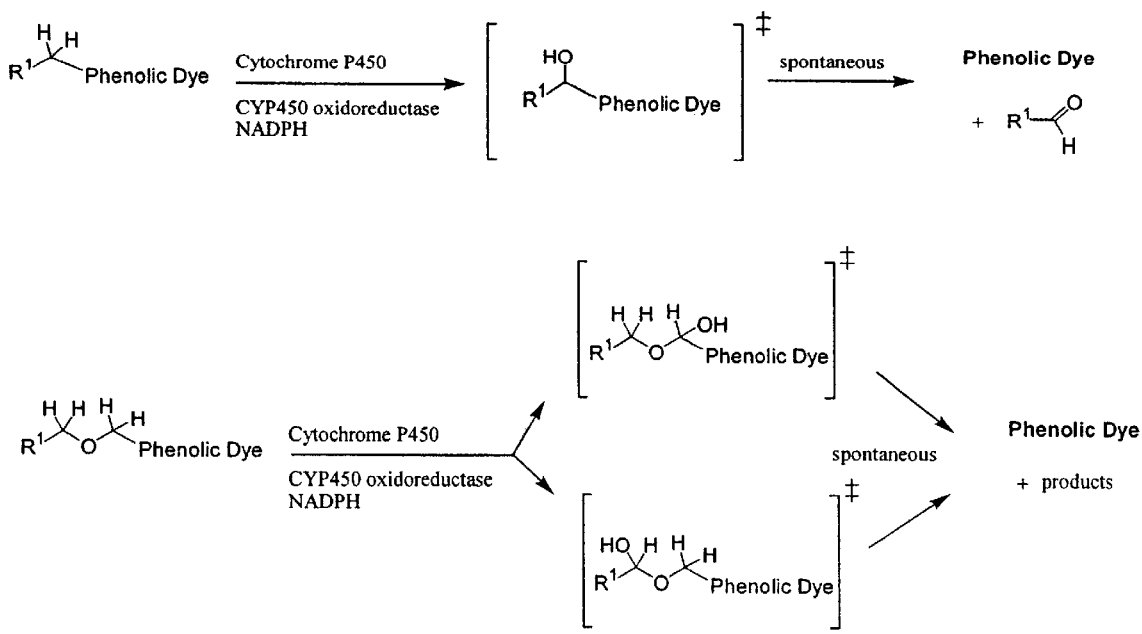
FIG. 3 illustrates Reaction Scheme 3, which compares the hydroxylation reaction that may lead to a free phenolic dye of a known optical CYP450 sensor (top) and an optical CYP450 sensor compound of the present invention (bottom).

According to present invention, FIG. 2 illustrates Reaction Scheme 2, which shows a generic structure of the optical CYP450 substrate/sensor of the present invention, and the CYP450-catalyzed hydroxylation reaction. FIG. 3 illustrates Reaction Scheme 3, which compares the hydroxylation reaction that may lead to a free phenolic dye of a known optical CYP450 sensor (top) and an optical CYP450 sensor compound of the present invention (bottom).

As herein described, candidate drugs can be screened and evaluated for their activities as substrates of or inhibitors of a CYP450 enzyme be using the optical CYP450 sensors of the present invention. A candidate drug may be determined to be an inhibitor or a substrate of a cytochrome P450 enzyme by contacting a cytochrome P450 enzyme with the candidate drug, under conditions suitable for interaction therebetween, providing at least one optical cytochrome P450 enzyme substrate, under conditions that would, in the absence of an inhibitor or substrate of the cytochrome P450 enzyme, be suitable for interaction between the optical cytochrome P450 enzyme substrate and the cytochrome P450 enzyme, and detecting the presence of signal of a free phenolic dye, wherein the phenolic dye would be, in the absence of an inhibitor of the cytochrome P450 enzyme, the product of the reaction between the cytochrome P450 enzyme and the optical cytochrome P450 enzyme substrate. Such efficient CYP450 substrates and inhibitors, as deemed appropriate by those of skill in the art, may be removed from a screening library where such efficient CYP450 substrates and inhibitors are not desired in the remainder of the screening for a candidate drug.

To distinguish between a substrate and an inhibitor of cytochrome P450 enzymes, typically, the candidate compound is incubated with at least one cytochrome P450 enzyme under conditions, which allow for metabolism of the candidate compound prior to providing the optical cytochrome P450 enzyme substrate under conditions that would, in the absence of an inhibitor or substrate of the cytochrome P450 enzyme, be suitable for interaction between the optical cytochrome P450 enzyme substrate and the cytochrome P450 enzyme. The resulting optical signal is compared to the one obtained from contacting a cytochrome P450 enzyme with the candidate drug, under conditions suitable for interaction therebetween, providing at least one optical cytochrome P450 enzyme substrate, under conditions that would, in the absence of an inhibitor of the cytochrome P450 enzyme, be suitable for interaction between the optical cytochrome P450 enzyme substrate and the cytochrome P450 enzyme. Metabolism of the candidate drug by a cytochrome P450 enzyme reduces its concentration in the assay medium and may lead to an apparent loss of cytochrome P450 inhibitory activity compared to conditions without metabolism of the compound which would indicate it was a substrate for the enzyme. An inhibitory compound that was not metabolized would show equal potency, irrespective of the time of addition of the optical cytochrome p450 enzyme substrate.

The following procedures may be used to then further screen, formulate, and administer the candidate drugs of the present invention. These drugs are within the present invention to the extent that they have not yet been identified as candidate drugs or modulators, and to the extent that they are identified as candidate drugs or modulators by means of using the optical sensors of the present invention.

In certain cases, a candidate drug may be determined to be a cytochrome P450 enzyme substrate of at least one cytochrome P450 enzyme, by selecting an optical cytochrome P450 enzyme substrate that is a derivative of the candidate drug; contacting a cytochrome P450 enzyme with the optical cytochrome P450 enzyme substrate under conditions suitable for interaction therebetween, and detecting the absence of signal of a free phenolic dye, that would be the product of the reaction between the cytochrome P450 enzyme and the optical cytochrome P450 enzyme substrate.

Bioavailability and Toxicology of Candidate Modulators

Once identified, candidate drugs or modulators can be further evaluated for bioavailability and toxicological effects using known methods. See Lu, Basic Toxicology, Fundamentals, Target Organs, and Risk Assessment, Hemisphere Publishing Corp., Washington (1985); U.S. Pat. No. 5,196,313 to Culbreth (issued Mar. 23, 1993) and U.S. Pat. No. 5,567,952 to Benet (issued Oct. 22, 1996). For example, toxicology of a candidate modulator can be established by determining in vitro toxicity towards a cell line, such as a mammalian i.e. human, cell line. Candidate modulators can be treated with, for example, tissue extracts, such as preparations of liver, such as microsomal preparations, to determine increased or decreased toxicological properties of the chemical after being metabolized by a whole organism. The results of these types of studies are often predictive of toxicological properties of chemicals in animals, such as mammals, including humans.

Such bioavailability and toxicological methods can be performed as part of or as complimentary to the screening systems and methods of the present invention. Such methods include contacting a sample having a target with at least one photon producing agent, at least one photon reducing agent, and a test chemical. An optical signal from said at least one photon producing agent is detected, wherein said optical signal is related to a toxicological activity. Bioavailability is any known in the art and can be detected, for example by measuring reporter genes that are activated during bioavailability criteria. Toxicological activity is any known in the art, such as apoptosis, cell lysis, crenation, cell death and the like. The toxicological activity can be measured using reporter genes that are activated during toxicological activity or by cell lysis (see WO 98/13353, published Apr. 2, 1998). Preferred reporter genes produce a fluorescent or luminescent translational product (such as, for example, a Green Fluorescent Protein (see, for example, U.S. Pat. No. 5,625,048 to Tsien et al., issued Apr. 29, 1998; U.S. Pat. No. 5,777,079 to Tsien et al., issued Jul. 7, 1998; WO 96/23810 to Tsien, published Aug. 8, 1996; WO 97/28261, published Aug, 7, 1997; PCT/US97/12410, filed Jul. 16, 1997; PCT/US97/14595, filed Aug. 15, 1997)) or a translational product that can produce a fluorescent or luminescent product (such as, for example, beta-lactamase, e.g., U.S. Pat. No. 5,741,657 to Tsien, issued Apr. 21, 1998, and WO 96/30540, published Oct. 3, 1996), such as an enzymatic degradation product. Cell lysis can be detected in the present invention as a reduction in a fluorescence signal from at least one photon-producing agent within a cell in the presence of at least one photon reducing agent. Such toxicological determinations can be made using prokaryotic or eukaryotic cells, optionally using toxicological profiling, such as described in PCT/US94/00583, filed Jan. 21, 1994, German Patent No 69406772.5-08, issued Nov. 25, 1997; EPC 0680517, issued Nov. 12, 1994; U.S. Pat. No. 5,589,337, issued Dec. 31, 1996; EPO 651825, issued Jan. 14, 1998; and U.S. Pat. No. 5,585,232, issued Dec. 17, 1996).

Alternatively, or in addition to these in vitro studies, the bioavailability and toxicological properties of a candidate modulator in an animal model, such as mice, rats, rabbits, or monkeys, can be determined using established methods. See, Lu, supra (1985); and Creasey, *Drug Disposition in Humans, The Basis of Clinical Pharmacology*, Oxford University Press, Oxford (1979), Osweiler, *Toxicology*, Williams and Wilkins, Baltimore, Md. (1995), Yang, *Toxicology of Chemical Mixtures*, $_{13}$ Case Studies, Mechanisms, and Novel Approaches,Academic Press, Inc., San Diego, Calif. (1994), Burrell et al., *Toxicology of the Immune System; A Human Approach*, Van Nostrand Reinhld, Co. (1997), Niesink et al., *Toxicology; Principles and Applications*, CRC Press, Boca Raton, Fla. (1996). Depending on the toxicity, target organ, tissue, locus, and presumptive mechanism of the candidate modulator, the skilled artisan would not be burdened to determine appropriate doses, $LD_{50}$ values, routes of administration, and regimes that would be appropriate to determine the toxicological properties of the candidate modulator. In addition to animal models, human clinical trials can be performed following established procedures, such as those set forth by the United States Food and Drug Administration (USFDA) or equivalents of other governments. These toxicity studies provide the basis for determining the undesired effects of a candidate modulator in vivo.

Efficacy of Candidate Modulators

Efficacy of a candidate modulator can be established using several art recognized methods, such as in vitro methods, animal models, or human clinical trials, see, Creasey, supra (1979). Recognized in vitro models exist for several diseases or conditions. For example, the ability of a chemical to extend the life-span of HIV-infected cells in vitro is recognized as an acceptable model to identify chemicals expected to be efficacious to treat HIV infection or AIDS, see, Daluge et al., *Antimicro. Agents Chemother.* 41:1082–1093 (1995). Furthermore, the ability of cyclosporin A (CsA) to prevent proliferation of T-cells in vitro has been established as an acceptable model to identify chemicals expected to be efficacious as immunosuppressants, see, Suthanthiran et al., supra, (1996). For nearly every class of therapeutic, disease, or condition, an acceptable in vitro or animal model is available. Such models exist, for example, for gastrointestinal disorders, cancers, cardiology, neurobiology, and immunology. In addition, these in vitro methods can use tissue extracts, such as preparations of liver, such as microsomal preparations, to provide a reliable indication of the effects of metabolism on the candidate modulator. Similarly, acceptable animal models may be used to establish efficacy of chemicals to treat various diseases or conditions. For example, the rabbit knee is an accepted model for testing chemicals for efficacy in treating arthritis. See Shaw and Lacy, *J. Bone Joint Surg. (Br)* 55:197–205 (1973)). Hydrocortisone, which is approved for use in humans to treat arthritis, is efficacious in this model which confirms the validity of this model. See, McDonough, *Phys. Ther.* 62:835–839 (1982). When choosing an appropriate model to determine efficacy of a candidate modulator, the skilled artisan can be guided by the state of the art to choose an appropriate model, dose, and route of administration, regime, and endpoint and as such would not be unduly burdened.

In addition to animal models, human clinical trials can be used to determine the efficacy of a candidate modulator in humans. The USFDA, or equivalent governmental agencies, have established procedures for such studies, see, e.g., http://www/fda.gov.

Selectivity of Candidate Modulators

The in vitro and in vivo methods described above as part of the present invention also establish the selectivity of a candidate drug or modulator. It is recognized that chemicals can modulate a wide variety of biological processes or be selective. Panels of cells based on the present invention can be used to determine the specificity of the candidate modulator. Selectivity is evident, for example, in the field of chemotherapy, where the selectivity of a chemical to be toxic towards cancerous cells, but not towards non-cancerous cells, is obviously desirable. Selective modulators are preferable because they have fewer side effects in the clinical setting. The selectivity of a candidate modulator can be established in vitro by testing the toxicity and effect of a candidate modulator on a plurality of cell lines that exhibit a variety of cellular pathways and sensitivities. The data obtained from these in vitro toxicity studies can be extended animal model studies, including human clinical trials, to determine toxicity, efficacy, and selectivity of the candidate modulator.

The Identification of Chemical, Modulator, or Therapeutic Compositions.

The invention includes compositions, such as novel chemicals, and therapeutics identified by at least one method of the present invention as having activity as either a CYP450 substrate or inhibitor by the operation of methods, systems or components described herein. Novel chemicals, as used herein, do not include chemicals already publicly known in the art to be useful drugs or modulators as of the filing date of this application. Typically, a chemical would be identified as having CYP450 activity from using the present invention and then its structure revealed from a proprietary database of chemical structures or determined using analytical techniques such as mass spectroscopy.

One embodiment of the invention is a chemical with useful activity, comprising a chemical identified by the method herein described. Such compositions include small organic molecules, nucleic acids, peptides and other molecules readily synthesized by techniques available in the art and developed in the future. For example, the following combinatorial compounds are suitable for screening as candidate drugs: peptoids (PCT Publication No. WO 91/19735, Dec. 26, 1991), encoded peptides (PCT Publication No. WO 93/20242, Oct. 14, 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., Proc. Nat. Acad. Sci. USA 90: 6909–6913 (1993)), vinylogous polypeptides (Hagihara et al., J. Amer. Chem. Soc. 114: 6568 (1992)), nonpeptidal peptidomimetics with a Beta-D-Glucose scaffolding (Hirschmann, R. et al., J. Amer. Chem. Soc. 114: 9217–9218 (1992)), analogous organic syntheses of small compound libraries (Chen, C. et al., J. Amer. Chem. Soc. 116:2661 (1994)), oligocarbamates (Cho, C. Y. et al., Science 261: 1303 (1993)), and/or peptidyl phosphonates (Campbell, D. A. et al., J. Org. Chem. 59: 658 (1994)). See, generally, Gordon, E. M. et al., J. Med Chem. 37: 1385 (1994). The contents of all of the aforementioned publications are incorporated herein by reference.

The present invention also encompasses the compositions, identified by the methods of the present invention, in a pharmaceutical compositions comprising a pharmaceutically acceptable carrier prepared for storage and subsequent administration, which have a pharmaceutically effective amount of the products disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

These compositions may be formulated and used as tablets, capsules or elixirs for oral administration; suppositories for rectal administration; sterile solutions, suspensions for injectable administration; and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes), may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods of the invention, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage for the products of the present invention can range broadly depending upon the desired affects and the therapeutic indication. Typically, dosages may be between about 10 microg/kg and 100 mg/kg body weight, preferably between about 100 microg/kg and 10 mg/kg body weight. Administration is preferably oral on a daily basis.

The exact formulation, route of administration and dosage can be chosen by the individual physician in view of the patient's condition. See e.g., Fingl et al., in The Pharmacological Basis of Therapeutics, 1975. It should be noted that the attending physician would know how to and when to terminate, interrupt, or adjust administration due to toxicity, or to organ dysfunctions. Conversely, the attending physician would also know how to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. A variety of techniques for formulation and administration may be found in Remington's Pharmaceutical Sciences, 18th Ed., Mack Publishing Co., Easton, Pa. (1990). Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Pharmaceutical compositions suitable for use as herein described include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping, or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Such formulations can be made using methods known in the art (see, for example, U.S. Pat. No. 5,733,888 (injectable compositions); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations).

The following examples are meant to describe the inventors' preferred modes of carrying out the invention, i.e., of preparing, characterizing, and using the preferred embodiments of the invention. Variations in the details of the particular methods employed and of the precise chemical compositions employed will undoubtedly be appreciated by those of skill in the art.

EXAMPLE 1

Synthesis of Fluorogenic Substrates for CYP450

Preparation of Benzyloxymethylresorufin (BOMR)

For all syntheses of the compounds of the invention, as herein described in this and the following EXAMPLES, the following protocols were (or are, with respect to EXAMPLE 7) followed unless so stated: Reaction conditions were (or are) carried out under atmospheric nitrogen. All solvents utilized were dried over 3 Å molecular sieves. All chemicals and reagents were used as purchased without further purification unless stated. Benzylchloromethylether was purchased from Fluka Chemie AG, Resorufin was purchased form Aldrich Chemical Co., 7-Hydroxy-3-trifluoromethycoumarin and 7-Hydroxy-3-cyanocoumarin were purchased from Molecular Probes and all were used as received. See also Wolfbeis, Otto, Z. Naturforsch. (1977) 32a, 1065–1067. Column chromatography was executed with J. T. Baker silica gel (particle size=0.04–0.061 mm) using solvent combinations determined via initial TLC analysis with Merck Kieselgel 60 $F_{254}$, precoated silica gel plates. The $^1$H NMR spectra, recorded at 500 MHz, were analyzed by NuMega Resonance Labs, Inc. Mass spectra were measured by ESI with a PE-SCIEX API 150EX.

Benzyloxymethylresorufin (BOMR) was prepared as follows: A suspension of resorufin, sodium salt, (235 mg, 1 mmol) and $K_2CO_3$ (248 mg, 1.5 mmol) in DMF (15 mL) was vigorously stirred at 0–5° C. for 25 min. Benzylchloromethylether (2.32 mL, 10.0 mmol), was then added quickly to the reaction mixture. The dark red mixture was stirred at 0° C. for 1.5 hrs. After which time the reaction turned to an orange solution. The reaction was monitored to completeness by TLC ($R_f$=0.42, 1:1 EtOAc:Hex.and $R_f$=0.05, CHCl$_3$). The reaction was then brought up in Et$_2$O (35 mL), and extracted with saturated NaHCO$_3$ (30 mL). The aqueous layer was extracted two more times with Et$_2$O (30 mL). The etheral and the resorufin bilayer was then combined and filtered through celite. The filtrate was then dried with anhydrous NaSO$_4$ and evaporated under reduced pressure. Chromatography of the crude product on silica gel (gradient 0–5% MeOH in CHCl$_3$) gave the pure Benzyloxymethyloxyresorufin as an orange solid (106 mg, 32%). $^1$H NMR (500 MHz, CDCl$_3$): δ 4.74 (s, 2H), 5.39 (s, 2H), 6.32 (s, 1H), 6.85–6.83 (m, 1H), 7.06–7.09 (m, 2H), 7.30–7.37(m, 5H), 7.42 (d, 1H), 7.72(d, 1H).

EXAMPLE 2

Preparation of 7-Benzyloxymethyloxy-3-cyanocoumarin (BOMCC)

7-Benzyloxymethyloxy-3-cyanocoumarin (BOMCC) was prepared as follows:
A mixture of 7-Hydroxy-3-cyanocoumarin$_1$, (187 mg, 1 mmol) and $K_2CO_3$ (248 mg, 1.5 mmol), in DMF (15 mL) was vigorously stirred at 0° C. for 25 min. Benzylchloromethylether (2.32 mL, 10.0 mmol), was then added quickly to the reaction. The bright yellow mixture was stirred at 0° C. for 45 min. After which time the reaction turned to a colorless solution. The reaction was monitored to completeness by TLC ($R_f$=0.5, 1:1 EtOAc:Hex.and $R_f$=0.24, CHCl$_3$). The reaction was then brought up in Et$_2$O (35 mL), and extracted with saturated NaHCO$_3$ (30 mL). The aqueous layer was extracted two more times with Et$_2$O (30 mL). The etheral layer was then combined then dried with anhydrous NaSO$_4$ and evaporated under reduced pressure. Chromatography of the crude product on silica gel (gradient 0–5% MeOH in CHCl$_3$) gave the pure 7-Benzyloxymethyloxy-3-cyanocoumarin as a white solid (9.21 mg, 3%). $^1$H NMR (500 MHz, CDCl$_3$): δ 4.73 (s, 2H), 5.39 (s, 2H), 7.08 (m, 2H), 7.32 (m, 5H), 7.49 (d, 1H), 8.17 (s, 1H).

EXAMPLE 3

Preparation of 7-(p-methoxybenzyloxy-4-trifluorocoumarin (MOBFC)

7-(p-methoxybenzyloxy-4-trifluorocoumarin (MOBFC) was prepared as follows: A mixture of 7-Hydroxy-3-trifluoromethycoumarin, (230 mg, 1 mmol), $K_2CO_3$ (248 mg, 1.5 mmol), and KI (1.66 g, 10 mmol) in DMF (15 mL) was vigorously stirred at 25° C. for 25 min. Paramethoxybenzylchloride (1.35 mL, 10.0 mmol), was then added quickly to the reaction. The bright yellow mixture was stirred at 25° C. for 1 hr. After which time the reaction turned to a colorless solution. The reaction was monitored to completeness by TLC $R_f$=0.67, 1:1 EtOAc:Hex.and $R_f$=0.3 CHCl$_3$). The reaction was then brought up in Et$_2$O (35 mL), and extracted with saturated NaHCO$_3$ (30 mL). The aqueous layer was extracted two more times with Et$_2$O (30 mL). The etheral layer were combined then dried with anhydrous NaSO$_4$ and evaporated under reduced pressure. Chromatography of the crude product on silica gel (gradient 0–5% MeOH in CHCl$_3$) gave the pure 7-Paramethoxybenzyl-4- trifluorocoumarin as a white solid (280 mg, 80%). $^1$H NMR (500 MHz, CDCl$_3$): δ 3.83 (s, 3H), 5.08 (s, 2H), 6.62 (s, 1H), 6.94 (m, 4H), 7.39 (m, 2H), 7.62 (m, 1H).

EXAMPLE 4

Preparation of Octyloxymethylresorufin (OOMR)

Octyloxymethylresorufin (OOMR) was prepared as follows: A suspension of resorufin, sodium salt, (235 mg, 1 mmol) and K$_2$CO$_3$ (248 mg, 1.5 mmol) in DMF (15 mL) was vigorously stirred at 0–5° C. for 25 min. Bromomethyl octyl ether (2.20 mL, 10.0 mmol), was then added quickly to the reaction mixture. The reaction was stirred at 0–5° C. for 1.5 h during which time, the dark red reaction mixture turned to an orange solution. The reaction was allowed to continue to stir at 0–5° C. while monitoring by TLC (Rf= 0.44, 1:1 EtOAc:Hex.and Rf=0.05, CHCl3) and stopped at the time when product decomposition was detected. The reaction was then brought up in Et$_2$O (35 mL), extracted with 30 mL of a saturated NaHCO$_3$ solution. The aqueous layer was extracted two more times with Et$_2$O (30 mL), the ether fractions were then combined and filtered through celite. The filtrate was then dried with anhydrous NaSO$_4$ and evaporated under reduced pressure. Chromatography of the crude product on silica gel (gradient 0–5% MeOH in CHCl$_3$) yielded 62 mg of the purified octyloxy-methylresorufin (OOMR) as an orange solid. $^1$H NMR (500 MHz, C δ 0Cl$_3$): δ 83 (t, 3H), 1.21–1.31 (m, 12H), 3.68 (t, 2H), 5.31 (s, 1H), 6.32 (s, 1H), 6.83 (dd, 1H), 7.02–7.06 (m, 2H), 7.42 (d, 1H), 7.72(d, 1H).

EXAMPLE 5

Preparation of 7-Methyloxymethyloxy-4-trifluorocoumarin (MOMFC)

7-Methyloxymethyloxy-4-trifluorocoumarin (MOMFC) was prepared as follows: A mixture of 7-hydroxy-4-trifluoromethylcoumarin (230 mg, 1 mmol) and K$_2$CO$_3$ (248 mg, 1.5 mmol), in DMF (15 mL) was vigorously stirred at 0–5° C. for 25 min. Bromomethyl methyl ether (0.97 mL, 10.0 mmol), was then added quickly to the reaction. The bright yellow mixture was stirred at 0–5° C. for 45 min during which time the reaction turned to a colorless solution. The reaction was allowed to continue to stir at 0–5° C. while monitoring by TLC (Rf=0.54, 1:1 EtOAc/:Hexane and Rf=0.24, CHCl$_3$) and stopped at the time when product decomposition was detected. The reaction was then brought up in Et$_2$O (35 mL), extracted with 30 mL of a saturated NaHCO$_3$ solution. The aqueous layer was extracted two more times with Et$_2$O (30 mL), the ether fractions were then combined, dried with anhydrous NaSO$_4$, filtered and evaporated under reduced pressure. Chromatography of the crude product on silica gel (gradient 0–5% MeOH in CHCl$_3$) gave 11 mg of the purified 7-methyloxymethyloxy-4-trifluoromethylcoumarin (MOMFC) as a white solid. $^1$H NMR (500 MHz, CDCl$_3$): δ 03.49 (s, 3H), 5.26 (s, 2H), 6.64 (s, 1H), 7.08–7.02 (m, 2H), 7.64 (d, 1H).

EXAMPLE 6

Preparation of Paramethoxybenzylresorufin (MOBR)

Paramethoxybenzylresorufin (MOBR) was prepared as follows: A mixture of resorufin, sodium salt, (235 mg, 1 mmol) and K$_2$CO$_3$ (248 mg, 1.5 mmol) in DMF (15 mL) was vigorously stirred at 0° C. for 25 min. Paramethoxy-benzylchloride (1.35 mL, 10.0 mmol), was then added quickly to the reaction. The dark red mixture was stirred at 25° C. for 1.5 hrs. After which time the reaction turned to an orange solution. The reaction was monitored to completeness by TLC (R$_f$=0.32, 1:1 EtOAc:Hex.and R$_f$=0.05, CHCl$_3$). The reaction was then brought up in Et$_2$O (35 mL), and extracted with saturated NaHCO$_3$ (30 mL). The aqueous layer was extracted two more times with Et$_2$O (30 mL). The etheral and the resorufin bilayer was then combined and filtered through celite. The filtrate was then dried with anhydrous NaSO$_4$ and evaporated under reduced pressure. Chromatography of the crude product on silica gel (gradient 0–5% MeOH in CHCl$_3$) gave the pure Paramethoxybenzyl-resorufin as an orange solid (60 mg, 18%). $^1$H NMR (500 MHz, CDCl$_3$): δ 3.83 (s, 3H), 5.10 (s, 2H), 6.32 (s, 1H), 6.82–6.88 (m, 2H), 6.94 (d, 2H), 6.99–7.01 (dd, 1H), 7.37 (d, 2H), 7.42 (d, 1H), 7.70(d, 1H).

EXAMPLE 7

Preparation of Other Optical CYP450 Sensors of the Invention

The following reaction schemes are used to synthesize other optical CYP450 sensors of the present invention:

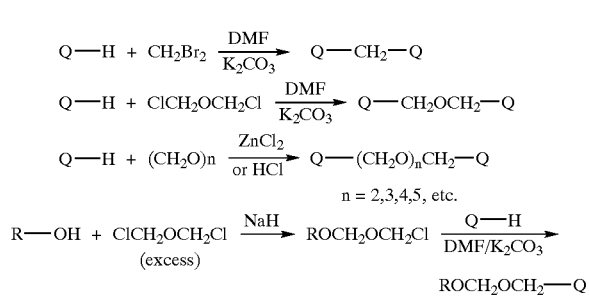

EXAMPLE 8

Kinetics of Benzyl-oxymethylresorufin (BOMR) Toward CYP 3A4

Applying the present invention to "modify" benzylresorufin (BR) leads, in one embodiment of the invention, to a compound of the invention, benzyl-oxymethylresorufin (BOMR), which has the following structure:

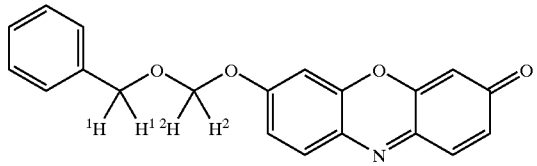

Whichever of the four abstractable hydrogen atoms (designated H$^1$ and H$^2$ in this representation of BOMR) is removed in the initial reaction step, with reference to Reaction Scheme 1 of FIG. 1, the hydroxylation product will spontaneously decompose to the free resorufin dye. In addition, the benzyloxy group, attached to the carbon carrying the two hydrogens designated H$^2$, contributes an inductive electronic effect on that carbon, which can stabilize the radical formed during abstraction of one of the H$^2$ hydrogens by a cytochrome P450. This new CYP450 substrate of the invention, BOMR, has a number of advantages over benzylresorufin as a substrate of CYP 3A4, as has been demonstrated and illustrated in FIG. 4. The data illustrated in FIG. 4 were acquired according to the method described in Henderson, P. J. F., *Statistical Analysis of Enzyme Kinetic Data,* "Enzyme Assays," Oxford University Press, 277–313 (1993).

Optimization of assay conditions was, and is preferably, accomplished through statistically validated Design of Experiments methodologies, using the commercial software package "Design-Expert®" produced by Stat-Ease® Inc. The data shown in FIGS. 4 and 5 were obtained with initial optimization.

Figure 4:
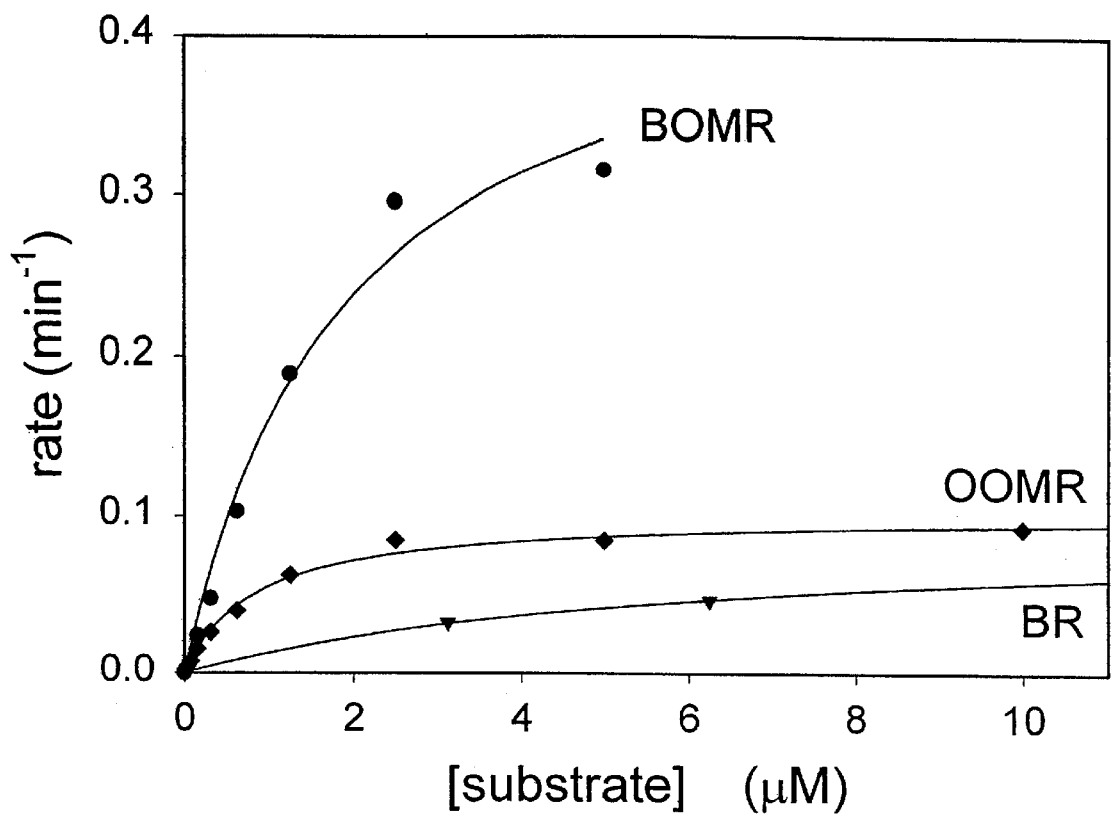
FIG. 4 illustrates a plot of the rate of resorufin ether conversion by CYP 3A4 as a function of CYP450 substrate concentration for the CYP450 substrate compounds of the invention, benzyloxymethylresorufin (BOMR) (circles) and n-octyloxymethylresorufin (OOMR) (diamonds), and as a function of resorufin benzyl ether (BR) (triangles).

By analyzing the data illustrated in FIG. 4, it was determined the that the CYP 3A4 turnover rate of BOMR is approximately five times greater than the CPY 3A4 turnover rate of BR; the BOMR turnover rate ($k_{cat}$) was 0.5 s$^{-1}$ ($K_m$ of 1.9 $\mu$M), whereas the BR turnover rate ($k_{cat}$) was 0.10 min$^{-1}$ ($K_m$=5.3 $\mu$M). Based on the calculated turnover rates and $K_m$ values, it was also determined that the enzymatic efficiency ($k_{cat}/K_m$) of CYP 3A4 towards BOMR was 14 times higher than the enzymatic efficiency ($k_{cat}/K_m$) of CYP 3A4 towards BR.

EXAMPLE 9

Detecting the Presence of CYP450 Inhibitors
Inhibition Assays

Figure 5:
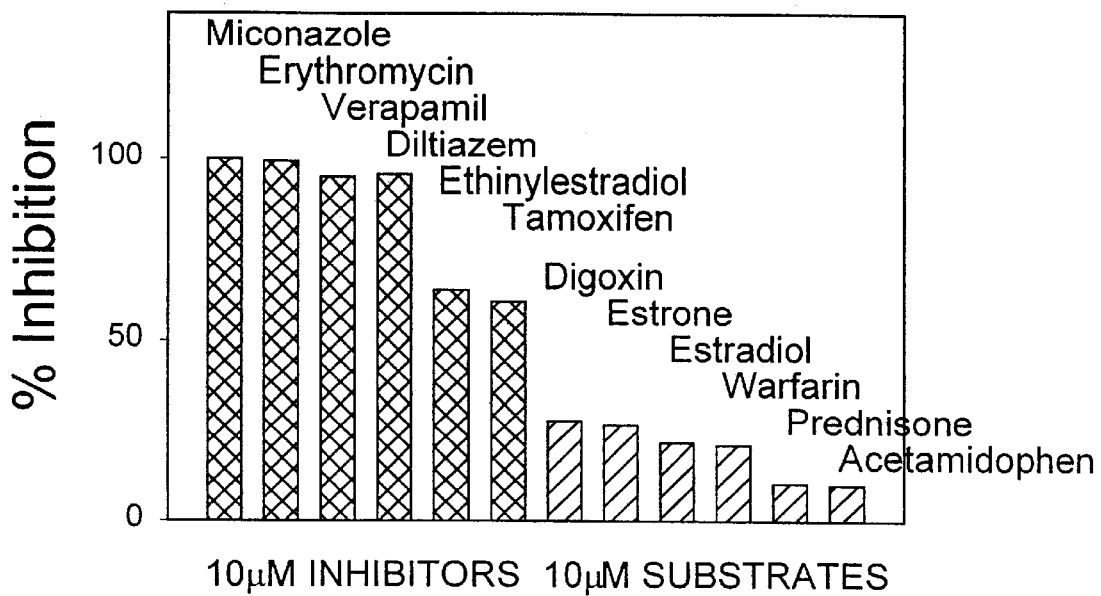
FIG. 5 illustrates a plot of percent CYP 3A4 inhibition as a function of the presence of selected inhibitors and drug substrates of CYP 3A4, and demonstrates the effect that these inhibitors (cross-hatched bars) and drug substrates (diagonal striped bars) had on the turnover rate of a compound of the invention, benyloxymethyl ether (BOMR), by the CYP 3A4 enzyme. This figure illustrates that inhibitors depress the rate of BOMR turnover more than approximately 50%, while drug substrates slow the rate of BOMR turnover up to approximately 30%.

To demonstrate to effectiveness of BOMR as a sensor for a specific subfamily of human CYP450, CYP 3A4 was incubated with 10 $\mu$M concentrations of various known inhibitors and drug substrates and BOMR was used to assess residual CYP450 activity in a typical screening format. As shown in FIG. 5, a CYP 3A4 inhibition assay using BOMR was conducted. This assay was performed in a 96-well plate at room temp and at a volume of 100 $\mu$M/well. 1.82× enzyme buffer was prepared and 55 $\mu$l was added to each well on the plate, for final assay concentrations 1.3 mM NADP+, 3.3 mM glucose-6-phosphate, 0.4 units/ml glucose-6-phosphate dehydrogenase and 10 mM MgCl2 in 100 mM K+ phosphate, pH 8.0. The drug inhibitors, miconazole, erythromycin, verapamil, diltiazem, ethinylestradiol, tamoxifen, and the substrates, digoxin, estrone, estradiol, warfarin, prednisone, and acetamidophen, were diluted from stock solutions of 10 mM in acetonitrile to 100 $\mu$M in 100 mM K+ phosphate. 10 $\mu$l of this dilution were added to appropriate wells on the plate for a final inhibitor concentration of 10 $\mu$M. The CYP 3A4 was diluted to yield a solution containing 2 pmol/10 ul in 100 mM K+ phosphate buffer, and 10 $\mu$l was added to appropriate wells on plate. 20 $\mu$l buffer was added to wells containing standards. The drug inhibitors were allowed to pre-incubated with the CYP 3A4 enzyme for 1 hr prior to the addition of the BOMR substrate. The BOMR substrate was diluted to 4 $\mu$M (4× final assay concentration) in 100 mM K+ phosphate buffer, and 25 $\mu$l was added to appropriate wells on the plate.

Data for a product fluorescence standard calibration curve was generated in the following manner. Resorufin was diluted to 40 $\mu$M in K+ phosphate buffer, and seven consecutive 1:2 dilutions were made. 25 $\mu$l of each dilution was added to the appropriate wells on the plate containing 75 $\mu$l of 100 mM K+ phosphate, pH 8.0, and reading of the plates was begun immediately. For BOMR, the excitation filter was 530 nm and the emission filter was 580 nm.

The results of these experiments are shown in FIG. 5. Compounds known to be effective inhibitors (e.g., miconazole and verapamil) inhibited the activity of CYP3A4 on BOMR by approximately 100%, effectively completely inhibiting the activity of CYP3A4 on BOMR.

Thus, as demonstrated with BOMR, and illustrated in FIGS. 4 and 5, introduction of the oxymethyl linker into fluorogenic substrates with long wavelength fluorophores, such as resorufin, yield the new CYP450 substrates of the invention with kinetic properties superior to those of the known, most closely-structurally related CYP450 substrates.

Figure 6:
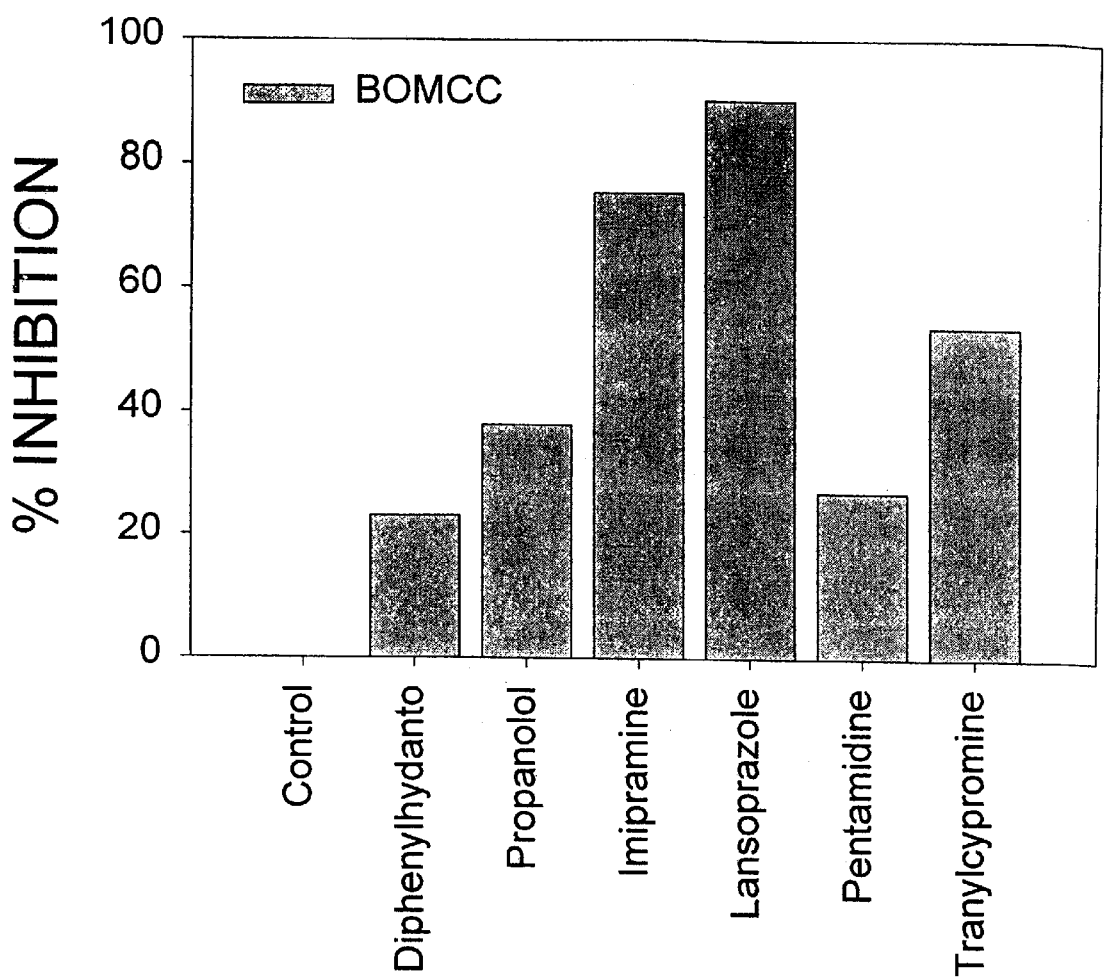
FIG. 6 illustrates a plot of percent CYP 2C19 inhibition as a function of the presence of various drugs at 10 $\mu$M concentrations that interact with CYP 2C19, and demonstrates that 7-benzyloxymethyloxy-3-cyanocoumarian (BOMCC) may be used as an optical CYP450 sensor to detect candidate drugs that interact with CYP 2C19.
Figure 7:
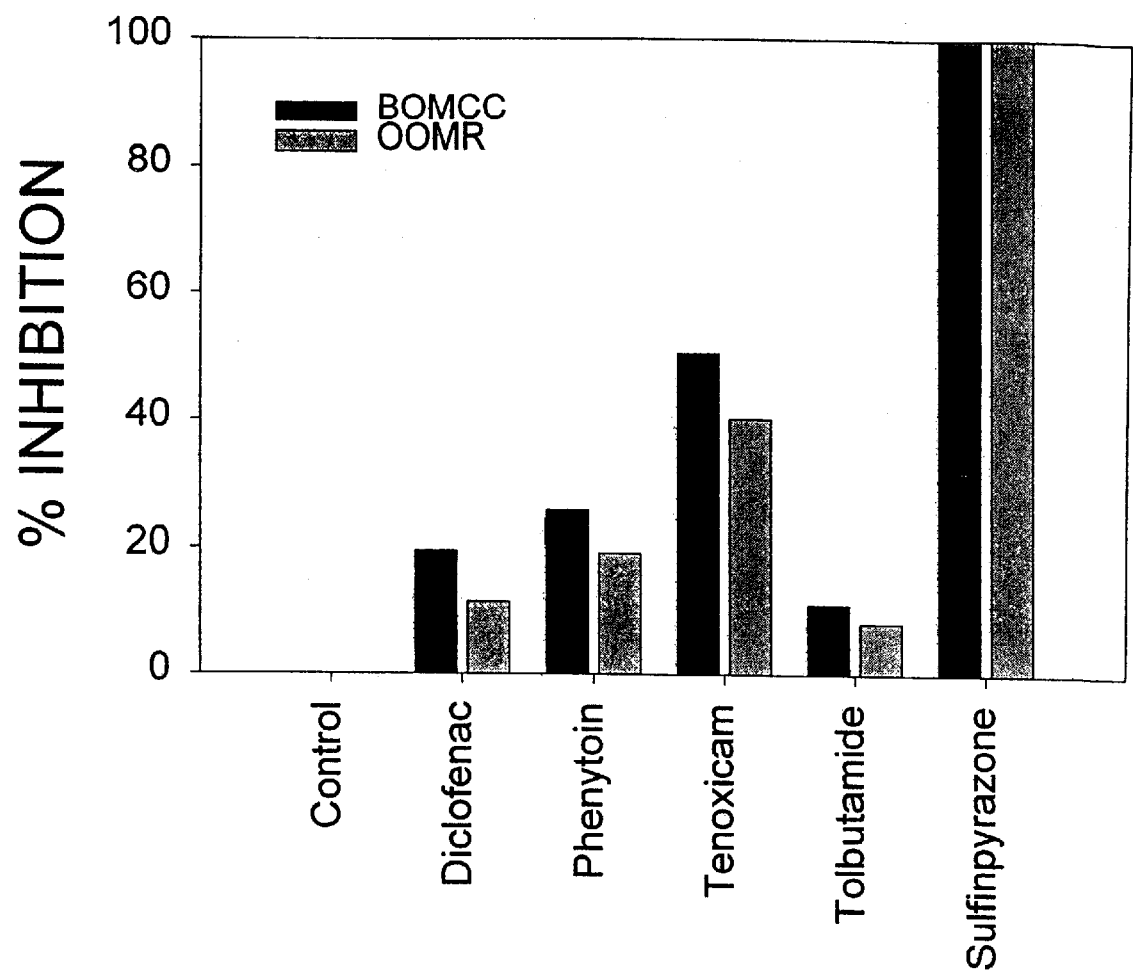
FIG. 7 illustrates a plot of percent CYP 2C9 inhibition as a function of the presence of various drugs at 10 $\mu$M concentrations that interact with CYP 2C9, and demonstrates that 7-benzyloxymethoxy-3-cyanocoumarian (BOMCC; dark bars) and octlyoxymethyl-resorufin (OOMR; light bars) may be used as an optical CYP450 sensor to detect drugs that interact with CYP 2C9.

The utility in detecting drug-CYP450 interactions of selected oxymethyl-linker containing substrates of the present invention was further demonstrated for 7-benzyloxymethoxy-3-cyanocoumarin (BOMCC), and resorrufin n-octyloxymethyl ether (OOMR), as illustrated in, respectively, FIG. 6, and FIGS. 6 and 7.

In FIG. 6, the results of a CYP 3A4 inhibition assay using BOMCC are illustrated. This FIG. illustrates that another compound of the invention, BOMCC, is useful as a means to detect the presence of inhibitors of the CYP450 enzyme CYP 3A4. This assay was performed in a 96-well plate at room temp and at a volume of 100 $\mu$l/well. 1.82× enzyme buffer was prepared and 55 $\mu$l was added to each well on the plate, for final assay concentrations of 1.3 mM NADP+, 3.3 mM glucose-6-phosphate, 0.4 units/ml glucose-6-phosphate dehydrogenase and 10 mM MgCl2 in 100 mM K+ phosphate, pH 8.0. The drug inhibitors, diphenylhydantoin, propanolol, imipramine, lansoprazole, pentamidine, and tranylcypromine, were diluted from stock solutions of 10 mM in acetonitrile to 100 $\mu$M in 100 mM K+ phosphate. 10 $\mu$l of this dilution was added to appropriate wells on the plate for a final inhibitor concentration of 10 $\mu$M. The CYP3A4 was diluted to a yield a solution containing 2 pmol/10 $\mu$l in 100 mM K+ phosphate buffer, and 10 $\mu$l was added to appropriate wells on the plate. 20 $\mu$l buffer was added to wells that contained standards. The drug inhibitors were allowed to pre-incubated with the 3A4 enzyme for 1 hr prior to the addition of the BOMCC substrate. The BOMCC substrate was diluted to 40 $\mu$M (4× final assay concentration) in 100 mM K+ phosphate buffer, pH 8.0, and 25 $\mu$l was added to appropriate wells.

Data for a product fluorescence standard calibration curve was generated in the following manner: 7-hydroxy-3-cyanocoumarin was diluted to 40 $\mu$M in K+ phosphate buffer, and seven consecutive 1:2 dilutions were made. 25 $\mu$l of each dilution was added to the appropriate wells on the plates containing 75 $\mu$l of 100 mM K+ phosphate, pH 8.0, and immediately begin reading the plates. For BOMCC, the excitation filter was 395 nm and the emission filter was 460 nm.

In FIG. 7, the results of a CYP 2C9 inhibition assay using two compounds of the invention, BOMCC and OOMR, are illustrated. This FIG. illustrates that BOMCC and OOMR are useful as means to detect the presence of inhibitors of the CYP450 enzyme 2C9. This assay was performed in a 96-well plate at room temperature and at a volume of 100 $\mu$l/well. 1.82× enzyme buffer was prepared and 55 $\mu$l was added to each well on the plate, for final assay concentrations 1.3 mM NADP+, 3.3 mM glucose-6-phosphate, 0.4 units/ml glucose-6-phosphate dehydrogenase and 10 mM MgCl2 in 100 mM K+ phosphate, pH 8.0. The drug inhibitors, diclofenac, phenytoin, tenoxicam, tolbutamide, and sulfinpyrazone, were diluted from stock solutions of 10 mM in acetonitrile to 100 $\mu$M in 100 mM K+ phosphate. 10 $\mu$l of this dilution was added to appropriate wells on the plate for a final inhibitor concentration of 10 $\mu$M. The CYP2C9 was diluted to a yield a solution containing 10 pmol/10 $\mu$l in 100 mM K+ phosphate buffer, and 10 $\mu$l was added to appropriate well on the plate. 20 $\mu$l buffer was added to wells that contain standards. The drug inhibitors were allowed to pre-incubated with the 2C9 enzyme for 1 hr prior to the addition of the BOMCC or OOMR substrate. The BOMCC substrate was diluted to 40 μM (4X final assay concentration) in 100 mM K+ phosphate buffer, pH 8.0, and 25 μl was added to the appropriate wells. The OOMR substrate was diluted to 8 μM (4× final assay concentration) in 100 mM K+ phosphate buffer, and 25 μl was added to appropriate wells on the plate. The standards 7-hydroxy-3-cyanocoumarin and resorufin were diluted to 40 μM in K+ phosphate buffer, to make seven 1:2 dilutions. 25 μl of each dilution was added to the appropriate wells on the plate containing 75 μl of 100 mM K+ phosphate, pH 8.0, and reading of the plates began immediately. For BOMCC, the excitation filter was 395 nm and the emission filter was 460 nm. For MOBR, the excitation filter was 530 nm and the emission filter was 580 nm.

EXAMPLE 10

Analysis of the Relative Kinetics of Fluorogenic Substrates of CYP 3A4

A variety of the oxymethyl containing substrates of the invention have been tested against known human CYP450 isozymes predominantly involved with drug metabolism in humans. New substrates suitable for high throughput screening were found for CYP 3A4, CYP 2C19, CYP 2C9, CYP 1A2 and CYP 2B6. Tables 1 through 9 as described in detail in this and the following EXAMPLES, provide data regarding the kinetic properties of various fluorogenic CYP450 substrates of the present invention, as contrasted to the kinetic properties of the most closely structurally-related, and currently-available, fluorogenic CYP450 substrates.

Table 1 has was prepared according to the general method described in Henderson, P. J. F., *Statistical Analysis of Enzyme Kinetic Data,* "Enzyme Assays," Oxford University Press, 277–313 (1993). The rows of Table 1 correspond to specific fluorogenic substrates tested against CYP 3A4; the columns correspond to, respectively, the abbreviations of the fluorogenic substrate, the chemical structure, the turnover rate at 10 μM, the turnover rate at 1.25 μM, $k_{cat}$, and $K_m$ values, the ratio of $k_{cat}$ and $K_m$ values, and the types of kinetics detected. For further understanding these terms in the context of this invention, attention is directed to FIG. 4 and the analysis of FIG. 4. As will be appreciated by those of skill in the art, the oxymethyl analogs of the present invention (BOMR, BOMFC, BOMCC, and EOMR) exhibited more efficient conversion to the same fluorescent product than each of the most closely, structurally-related substrates (respectively, BR, BFC, BCC, and ER). Indeed, in all cases presently studied, except for the case of one fluorogenic CYP450 substrate evaluated against one CYP450 enzyme (the effect of MOMFC as a substrate of CYP 2B6 as shown in Table 5), the oxymethyl derivatives of the present invention displayed improved kinetics over the most closely, structurally-related fluorogenic substrates.

TABLE 1

| 3A4 Abbr. | Substrate Structure | v (10 uM) (min-1) | v (1.25 uM) (min-1) | kcat (min-1) | Km (microM) | kcat/Km s-1/M | type of kinetics |
|---|---|---|---|---|---|---|---|
| BR | 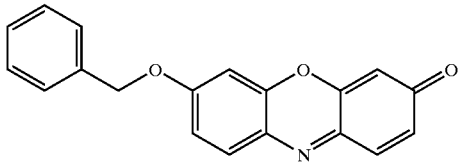 | 0.08 | 0.02 | 0.1 | 5.3 | 377 | Michaelis-Menten |
| BOMR | 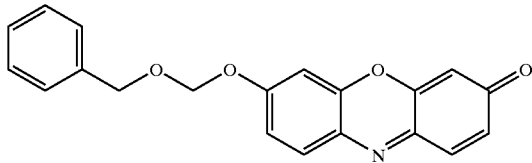 | 0.88 | 0.55 | 1.1 | 1.4 | 13095 | Michaelis-Menten |
| BFC | 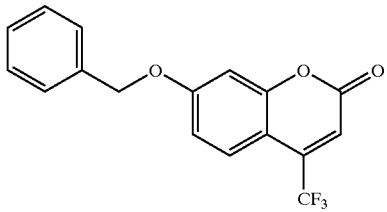 | 0.81 | 0.04 | n.a. | n.a. | n.a. | linear |
| BOMFC | 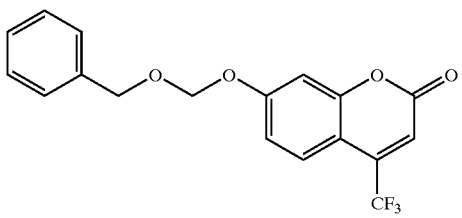 | 1.41 | 0.11 | 4.0 | 22.0 | 3030 | Michaelis-Menten |

TABLE 1-continued

| 3A4 Abbr. | Substrate Structure | v (10 uM) (min-1) | v (1.25 uM) (min-1) | kcat (min-1) | Km (microM) | kcat/Km s-1/M | type of kinetics |
|---|---|---|---|---|---|---|---|
| BCC | | — | — | — | — | — | — |
| BOMCC | | 0.98 | 0.12 | (10.0) | (89.0) | (1873) | sigmoidal |
| ER | | — | — | — | — | — | — |
| EOMR | | 0.10 | 0.03 | 0.1 | 4.5 | 489 | Michaelis-Menten |

Kinetic properties of fluorogenic substrates with CYP 3A4. Benzylresorufin (BR) and 7-Benzyloxy-4-trifluoromethylcoumarin (BFC) are commercially available CYP450 substrates. Their oxymethyl analogs (BOMR, BOMFC) are more efficiently converted to the corresponding fluorescent product. The oxymethyl analogs of 7-Benzyloxy-3-cyanocoumarin and of ethylresorufin are better substrates than the parent substrates. (uM=$\mu$M; n.a.= not applicable; — — — too low to quantify, ( ) from Michaelis-Menten fit)

EXAMPLE 11

Analysis of the Relative Kinetics of Fluorogenic Substrates of CYP 2C19

Table 2 was prepared according to the same general methodology of Table 1, the general method described in Henderson, P. J. F., *Statistical Analysis of Enzyme Kinetic Data*, "Enzyme Assays," Oxford University Press, 277–313 (1993). The rows of Table 2 correspond to specific fluorogenic substrates tested against CYP 2C19; the columns correspond to, respectively, the abbreviations of the fluorogenic substrate, the chemical structure, the turnover rate at 10 $\mu$M, the turnover rate at 1.25 $\mu$M, $k_{cat}$, and $K_m$ values, the ratio of $k_{cat}$ and $K_m$ values, and the types of kinetics detected. As will be appreciated by those of skill in the art, the oxymethyl analogs of the present invention (EOMCC, BOMCC, and MOMCC) exhibited more efficient conversion to the same fluorescent product than each of the most closely, structurally-related substrates (respectively, 3CEC, BCC, and 3CMC).

TABLE 2

| 2C19 Abbr. | Substrate Structure | v (10 uM) (min-1) | v (1.25 uM) (min-1) | kcat (min-1) | Km (microM) | kcat/Km s-1/M | type of kinetics |
|---|---|---|---|---|---|---|---|
| 3CEC | | 0.34 | 0.05 | 1.7 | 41.0 | 671 | Michaelis-Menten |

TABLE 2-continued

| 2C19 Abbr. | Substrate Structure | v (10 uM) (min-1) | v (1.25 uM) (min-1) | kcat (min-1) | Km (microM) | kcat/Km s-1/M | type of kinetics |
|---|---|---|---|---|---|---|---|
| EOMCC | | 2.22 | 0.34 | 5.7 | 16.6 | 5723 | Michaelis-Menten |
| BCC | | 0.06 | 0.02 | 0.1 | 6.4 | 234 | Michaelis-Menten |
| BOMCC | | 0.68 | 0.16 | 1.9 | 14.0 | 2262 | Michaelis-Menten |
| 3CMC | | 0.07 | 0.01 | n.a. | n.a. | n.a. | linear |
| MOMCC | | 0.38 | 0.14 | 0.5 | 3.2 | 2604 | Michaelis-Menten |

Kinetic properties of fluorogenic substrates with CYP2 C19. 3-Cyano-7-ethoxycoumarin (3CEC) is a commercially available CYP450 substrate. Its oxymethyl analog (EOMCC) is more efficiently converted to the corresponding fluorescent product. The oxymethyl analogs of 7-benzyloxy-3-cyanocoumanin and of 3-cyano-7-methoxycoumarin are better substrates than the parent substrates. (uM=$\mu$M; n.a.= not applicable; — — — too low to quantify, ( ) from Michaelis-Menten fit)

EXAMPLE 12

Analysis of the Relative Kinetics of Fluorogenic Substrates of CYP 2C9

Table 3 was prepared according to the same general methodology of Table 1, the general method described in Henderson, P. J. F., *Statistical Analysis of Enzyme Kinetic Data,* "Enzyme Assays," Oxford University Press, 277–313 (1993). The rows of Table 3 correspond to specific fluorogenic substrates tested against CYP 2C19; the columns correspond to, respectively, the abbreviations of the fluorogenic substrate, the chemical structure, the turnover rate at 10 $\mu$M, the turnover rate at 1.25 $\mu$M, $k_{cat}$, and $K_m$ values, the ratio of $k_{cat}$ and $K_m$ values, and the types of kinetics detected. As will be appreciated by those of skill in the art, the oxymethyl analogs of the present invention (MOMFC, BOMCC, and MOMCC) exhibited more efficient conversion to the same fluorescent product than each of the most closely, structurally-related substrates (respectively, MFC, BCC, and 3CMC).

TABLE 3

| 2C9 Abbr. | Substrate Structure | v (10 uM) (min-1) | v (1.25 uM) (min-1) | kcat (min-1) | Km (microM) | kcat/Km s-1/M | type of kinetics |
|---|---|---|---|---|---|---|---|
| MFC | | 0.03 | 0.01 | 0.4 | 103.0 | 70 | Michaelis-Menten |
| MOMFC | | 0.07 | 0.00 | 0.1 | 14.9 | 157 | Michaelis-Menten |
| BCC | | 0.00 | 0.00 | — | — | — | — |
| BOMCC | | 0.42 | 0.04 | 2.1 | 43.0 | 814 | Michaelis-Menten |
| 3CMC | | 0.04 | 0.00 | 0.4 | 70.9 | 85 | linear |
| MOMCC | | 0.07 | 0.01 | 0.2 | 20 | 167 | Michaelis-Menten |

Kinetic properties of fluorogenic substrates with CYP 2C9. 7-Methoxy-4-trifluoromethylcoumarin (MFC) is a commercially available CYP450 substrate. Its oxymethyl analog (MOMFC) is more efficiently converted to the corresponding fluorescent product. The oxymethyl analogs of 7-benzyloxy-3-cyanocoumarin and of 3-cyano-7-methoxycoumarin are better substrates than the parent substrates. (uM=$\mu$M; n.a.=not applicable; — — — too low to quantify, ( ) from Michaelis-Menten fit)

EXAMPLE 13

Analysis of the Relative Kinetics of Fluorogenic Substrates of CYP 1A2

Table 4 was prepared according to the same general methodology of Table 1, the general method described in Henderson, P. J. F., *Statistical Analysis of Enzyme Kinetic Data,* "Enzyme Assays," Oxford University Press, 277–313 (1993). The rows of Table 3 correspond to specific fluorogenic substrates tested against CYP 1A2; the columns correspond to, respectively, the abbreviations of the fluorogenic substrate, the chemical structure, the turnover rate at 10 $\mu$M, the turnover rate at 1.25 $\mu$M, $k_{cat}$, and $K_m$ values, the ratio of $k_{cat}$ and $K_m$ values, and the types of kinetics detected. As will be appreciated by those of skill in the art, the oxymethyl analog of the present invention (EOMCC) exhibited more efficient conversion to the same fluorescent product than each of the most closely, structurally-related substrates (3CEC).

TABLE 4

| 1A2 Abbr. | Substrate Structure | v (10 uM) (min-1) | v (1.25 uM) (min-1) | kcat (min-1) | Km (microM) | kcat/Km s-1/M | type of kinetics |
|---|---|---|---|---|---|---|---|
| 3CEC | 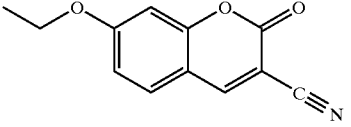 | 12.55 | 1.73 | 44.0 | 26.0 | 28205 | Michaelis-Menten |
| EOMCC | 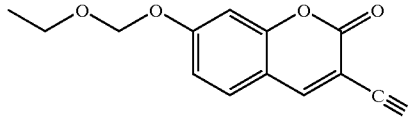 | 9.95 | 1.77 | 21.0 | 11.0 | 31818 | Michaelis-Menten |

Kinetic properties of fluorogenic substrates with CYP 1A2. 3-Cyano-7-ethoxycoumarin (3CEC) is a commercially available CYP450 substrate. Its oxymethyl analog (EOMCC) is converted to the corresponding fluorescent product a little bit more efficiently (greater $k_{cat}/K_m$).

EXAMPLE 14

Analysis of the Relative Kinetics of Fluorogenic Substrates of CYP 2B6

Table 5 was prepared according to the same general methodology of Table 1, the general method described in Henderson, P. J. F., *Statistical Analysis of Enzyme Kinetic Data*, "Enzyme Assays," Oxford University Press, 277–313 (1993). The rows of Table 5 correspond to specific fluorogenic substrates tested against CYP 2C19; the columns correspond to, respectively, the abbreviations of the fluorogenic substrate, the chemical structure, the turnover rate at 10 μM, the turnover rate at 1.25 μM, $k_{cat}$, and $K_m$ values, the ratio of $k_{cat}$ and $K_m$ values, and the types of kinetics detected. As will be appreciated by those of skill in the art, two of the oxymethyl analogs of the present invention test in this EXAMPLE (BOMCC and BOMR) exhibited more efficient conversion to the same fluorescent product than each of the most closely, structurally-related substrates (respectively, BCC, and BR).

As noted above, the case of MOMFC as a substrate of CYP 2B6 is the sole case in which the fluorogenic CYP450 substrate of the present invention did not exhibit improved kinetics, i.e., more efficient conversion to the same fluorescent product, than the most closely, structurally-related substrate, in that case MFC. By the method used to identify this sole case, or comparable methods for selecting fluorogenic CYP450 substrate and CYP450 enzyme pairs, those of skill in the art may distinguish the most desirable fluorogenic CYP450 substrates of the present invention for their particular use.

TABLE 5

| 2B6 Abbr. | Substrate Structure | v (10 uM) (min-1) | v (1.25 uM) (min-1) | kcat (min-1) | Km (microM) | kcat/Km s-1/M | type of kinetics |
|---|---|---|---|---|---|---|---|
| MFC | 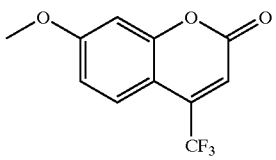 | 2.53 | 1.63 | 2.9 | 1.4 | 34524 | Michaelis-Menten |
| MOMFC | 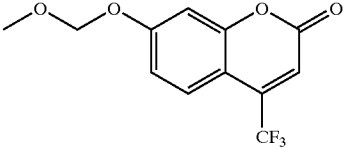 | 0.71 | 0.54 | n.a. | n.a. | n.a. | not Michaelis-Menten |
| BCC | 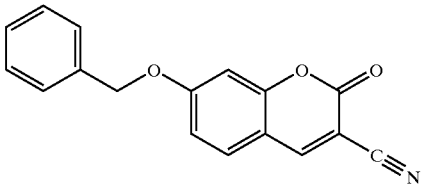 | 0.07 | 0.04 | 0.1 | 1.3 | 1064 | Michaelis-Menten |

TABLE 5-continued

| 2B6 Abbr. | Substrate Structure | v (10 uM) (min-1) | v (1.25 uM) (min-1) | kcat (min-1) | Km (microM) | kcat/Km s-1/M | type of kinetics |
|---|---|---|---|---|---|---|---|
| BOMCC | (structure) | 3.05 | 0.38 | 66.0 | 52.0 | 21154 | Michaelis-Menten |
| BR | (structure) | 0.42 | 0.42 | n.a. | n.a. | n.a. | not Michaelis-Menten |
| BOMR | (structure) | 0.71 | 0.28 | 0.8 | 0.73 | 18265 | Michaelis-Menten |

Kinetic properties of fluorogenic substrates with CYP 2B6. 7-Methoxy-4-trifluoromethylcoumarin (MFC) is a commercially available CYP450 substrate. This is the occasion on which the oxymethyl analog (MOMFC) is less efficiently converted to the corresponding fluorescent product found to date (Nov. 15, 1998). The oxymethyl analogs of 7-benzyloxy-3-cyanocoumarin and of benzylresorufin are better substrates than the parent substrates. (uM=$\mu$M; n.a.= not applicable; — — — too low to quantify, ( ) from Michaelis-Menten fit)

EXAMPLE 15

Analysis of the Relative Kinetics of Fluorogenic Substrates of CYP 3A4 and CYP 2D6

Table 6 was prepared according to the same general methodology of Table 1, the general method described in Henderson, P. J. F., *Statistical Analysis of Enzyme Kinetic Data*, "Enzyme Assays," Oxford University Press, 277–313 (1993). The rows of Table 6 correspond to specific fluorogenic substrates tested against CYP 3A4 and CYP 2D6, as indicated; the columns correspond to, respectively, the abbreviations of the fluorogenic substrate, the chemical structure, the turnover rate at 10 $\mu$M, the turnover rate at 1.25 $\mu$M, $k_{cat}$, and $K_m$ values, the ratio of $k_{cat}$ and $K_m$ values, and the types of kinetics detected.

TABLE 6

| | Substrate Structure | v (10 uM) (min-1) | v (1.25 uM) (min-1) | kcat (min-1) | Km (microM) | kcat/Km s-1/M |
|---|---|---|---|---|---|---|
| 3A4 Abbr. | | | | | | |
| OOMR | (structure) | 0.601 | 0.323 | 0.66 | 1.4 | 7857 |

TABLE 6-continued

| | | | | | | |
|---|---|---|---|---|---|---|
| BOM-DDAO | | 4.2041 | 0.4402 | 6 | 7 | 14286 |
| OOMCC | | 0.961 | 0.227444 | 1.19 | 4.4 | 4508 |
| MOMR | | 0.0338 | 0.0083 | 0.06 | 6 | 167 |
| BRCBE | | 0.6241 | 0.1992 | 0.83 | 2.7 | 5123 |
| MOBFC | | 0.3453 | 0.0214 | 0.7 | 13 | 897 |
| 2D6 Abbr. | | | | | | |
| MOMR | | 0.21457 | 0.03396 | 0.34 | 8 | 708 |
| MOBR | | 0.0409 | 0.0185 | 0.049 | 3.1 | 263 |
| IPCC | | 0.0378 | 0.0076 | 0.1 | 18 | 93 |

Other substrates first synthesized and tested on CYP 3A4 and CYP 2D6. Oxymethyl ether derivatives of the invention (OOMR, BOM-DDAO, OOMCC, MOMR;) are listed in bold; other ethers are listed in italics.

EXAMPLE 16

Analysis of the Relative Kinetics of Fluorogenic Substrates of CYP 2C9 and CYP 2C19

Table 7 was prepared according to the same general methodology of Table 1, the general method described in Henderson, P. J. F., *Statistical Analysis of Enzyme Kinetic Data,* "Enzyme Assays," Oxford University Press, 277–313 (1993). The rows of Table 7 correspond to specific fluorogenic substrates tested against CYP 2C9 and CYP 2C19, as indicated; the columns correspond to, respectively, the abbreviations of the fluorogenic substrate, the chemical structure, the turnover rate at 10 μM, the turnover rate at 1.25 μM, $k_{cat}$, and $K_m$ values, the ratio of $k_{cat}$ and $K_m$ values, and the types of kinetics detected.

TABLE 7

| | Substrate Structure | v (10 uM) (min-1) | v (1.25 uM) (min-1) | kcat (min-1) | Km (microM) | kcat/Km s-1/M |
|---|---|---|---|---|---|---|
| 2C9 Abbr. | | | | | | |
| OOMR | 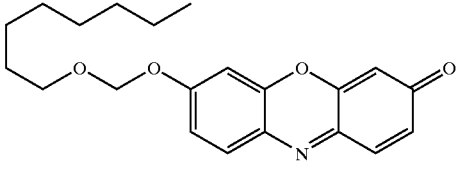 | 0.31 | 0.137 | 0.4 | 2.6 | 2564 |
| MOBFC | 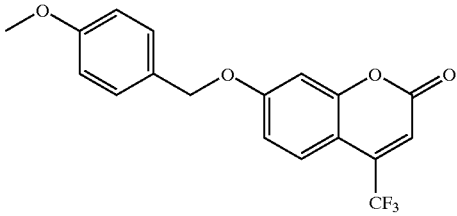 | 0.188 | 0.02 | 0.29 | 7.7 | 628 |
| 2C19 Abbr. | | | | | | |
| OOMCC | 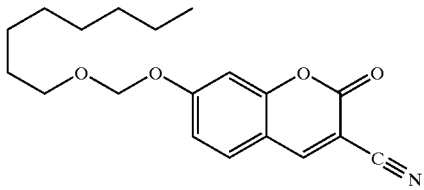 | 1.043 | 0.179 | 1.7 | 6.9 | 4106 |
| OOMR | 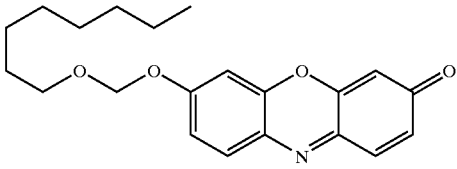 | 0.13 | 0.1 | 0.17 | 0.7 | 4048 |
| MOMR | 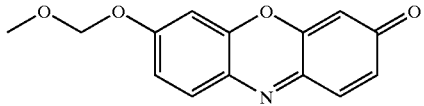 | 0.062 | 0.06 | n.d. | n.d. | n.d. |
| MOBR | 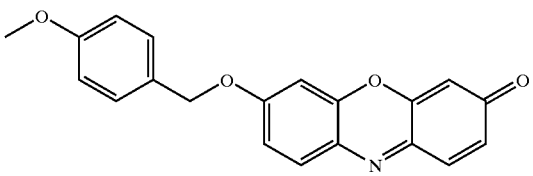 | 0.69 | 1.26 | n.d. | n.d. | n.d. |

TABLE 7-continued

| Abbr | Structure | | | | | |
|---|---|---|---|---|---|---|
| DMMC | [7-methoxy-4-(diethylaminomethyl)coumarin structure] | 0.23 | 0.03 | 0.4 | 8.5 | 784 |
| IPCC | [7-isopropoxy-3-cyanocoumarin structure] | 0.232 | 0.027 | 1.95 | 57.2 | 568 |

Other substrates first synthesized and tested on CYP 2C9 and CYP 2C19. Oxymethyl ether derivatives of the invention (OOMR, OOMCC, MOMR) are listed in bold; other ethers are listed italics.

EXAMPLE 17

Analysis of the Relative Kinetics of Fluorogenic Substrates of CYP 3A4 and CYP 2D6

Table 8 was prepared according to the same general methodology of Table 1, the general method described in Henderson, P. J. F., *Statistical Analysis of Enzyme Kinetic Data,* "Enzyme Assays," Oxford University Press, 277–313 (1993). The rows of Table 8 correspond to specific fluorogenic substrates tested against CYP 3A4 and CYP 2D6, as indicated; the columns correspond to, respectively, the abbreviations of the fluorogenic substrate, the chemical structure, the turnover rate at 10 $\mu$M, the turnover rate at 1.25 $\mu$M, $k_{cat}$, and $K_m$ values, the ratio of $k_{cat}$ and $K_m$ values, and the types of kinetics detected. As will be appreciated by those of skill in the art, the oxyphenylmethyl analogs of the present invention (MOBFC, MOBR) exhibited more efficient conversion to the same fluorescent product than each of the most closely, structurally-related substrates (respectively, MFC and MR). Indeed, in all cases presently studied, the oxyphenylmethyl derivatives of the present invention displayed improved kinetics over the most closely, structurally-related fluorogenic substrates.

TABLE 8

| | Substrate Structure | v (10 uM) (min-1) | v (1.25 uM) (min-1) | kcat (min-1) | Km (microM) | kcat/Km s-1/M | type of kinetics |
|---|---|---|---|---|---|---|---|
| 3A4 Abbr. | | | | | | | |
| MFC | [7-methoxy-4-trifluoromethylcoumarin structure] | — | — | — | — | — | — |
| MOBFC | [7-(4-methoxybenzyloxy)-4-trifluoromethylcoumarin structure] | 0.35 | 0.02 | 0.7 | 13.0 | 897 | Michaelis-Menten |

TABLE 8-continued

| 2D6 Abbr. | Structure | v (10 uM) (min-1) | v (1.25 uM) (min-1) | kcat (min-1) | Km (microM) | kcat/Km s-1/M | type of kinetics |
|---|---|---|---|---|---|---|---|
| MFC | 7-methoxy-4-trifluoromethylcoumarin | 0.10 | 0.03 | 0.3 | 10.0 | 417 | Michaelis-Menten |
| MOBFC | 7-(4-methoxybenzyloxy)-4-trifluoromethylcoumarin | 0.49 | 0.09 | 0.6 | 5.0 | 2067 | Michaelis-Menten |
| MR | methylresorufin | — | — | — | — | — | — |
| MOBR | (4-methoxybenzyloxy)resorufin | 0.04 | 0.02 | 0.0 | 3.1 | 263 | Michaelis-Menten |

Kinetic properties of fluorogenic substrates with CYP 3A4 and CYP 2D6. 7-Methoxy-4-trifluoromethylcoumarin (MFC) and Methylresorufin (MR) are commercially available CYP450 substrates. Their oxyphenylmethyl analogs (MOBFC and MOBR) are more efficiently converted to the corresponding fluorescent products. (uM=μM; n.a.=not applicable; — — — too low to quantify, ( ) from Michaelis-Menten fit)

EXAMPLE 18

Analysis of the Relative Kinetics of Fluorogenic Substrates of CYP 2C9, CYP 2C 19 And 2B6

Table 9 was prepared according to the same general methodology of Table 1, the general method described in Henderson, P. J. F., *Statistical Analysis of Enzyme Kinetic Data*, "Enzyme Assays," Oxford University Press, 277–313 (1993). The rows of Table 9 correspond to specific fluorogenic substrates tested against CYP 2C9 and CYP 2C19 and CYP 2B6, as indicated; the columns correspond to, respectively, the abbreviations of the fluorogenic substrate, the chemical structure, the turnover rate at 10 μM, the turnover rate at 1.25 μM, $k_{cat}$, and $K_m$ values, the ratio of $k_{cat}$ and $K_m$ values, and the types of kinetics detected. As will be appreciated by those of skill in the art, the oxyphenylmethyl analogs of the present invention (MOBFC, MOBR) exhibited more efficient conversion to the same fluorescent product than each of the most closely, structurally-related substrates (respectively, MFC and MR). Indeed, in all cases presently studied, the oxyphenylmethyl derivatives of the present invention displayed improved kinetics over the most closely, structurally-related fluorogenic substrates.

TABLE 9

| 2C9 Abbr. | Substrate Structure | v (10 uM) (min-1) | v (1.25 uM) (min-1) | kcat (min-1) | Km (microM) | kcat/Km s-1/M | type of kinetics |
|---|---|---|---|---|---|---|---|
| MFC | 7-methoxy-4-trifluoromethylcoumarin | 0.03 | not done | 0.4 | 103.0 | 70 | Michaelis-Menten |

TABLE 9-continued

| Abbr. | Structure | | | | | | |
|---|---|---|---|---|---|---|---|
| MOBFC | (4-methoxybenzyloxy-4-trifluoromethylcoumarin structure) | 0.19 | 0.02 | 0.3 | 7.7 | 628 | Michaelis-Menten |
| MR | (methylresorufin structure) | — | — | — | — | — | — |
| MOBR | (4-methoxybenzyloxy resorufin structure) | 0.02 | 0.02 | 0.0 | 0.4 | 952 | Michaelis-Menten |
| 2C19 Abbr. | | | | | | | |
| MR | (methylresorufin structure) | — | — | — | — | — | — |
| MOBR | (4-methoxybenzyloxy resorufin structure) | 0.69 | 1.26 | n.a. | n.a. | n.a. | not MMK |
| 2B6 Abbr. | | | | | | | |
| MR | (methylresorufin structure) | — | — | — | — | — | — |
| MOBR | (4-methoxybenzyloxy resorufin structure) | 0.10 | 0.08 | 0.4 | 0.1 | 58333 | Michaelis-Menten |

Kinetic properties of fluorogenic substrates with CYP 2C9, CYP 2C19 and CYP 2B6. 7-Methoxy-4-trifluoromethylcoumarin (MFC) and Methylresorufin (MR) are commercially available CYP450 substrates. Their oxyphenylmethyl analogs (MOBFC and MOBR) are more efficiently converted to the corresponding fluorescent products. (uM=$\mu$M; n.a.=not applicable; — — — too low to quantify, ( ) from Michaelis-Menten fit)

EXAMPLE 19

Determining the Apparent Inhibition Constants ($k_i$) of Drugs that Interact with CYP450 2D6

To demonstrate the effectiveness of MOBFC as a sensor for a specific subfamily of human CYP450, CYP 2D6 and its use in determining apparent inhibition constants following experiment was conducted. CYP 2D6 was incubated with 10 $\mu$M concentrations of various known inhibitors and drug substrates and residual CYP 2D6 activity assayed with the fluorogenic substrate MOBFC. The assay was performed in a 96-well plate at room temp and at a volume of 100 $\mu$l/well.

4× enzyme buffer was prepared and 25 µl was added to each well on the plate, for final assay concentrations of 3.3 mM glucose-6-phosphate, 0.4 units/ml glucose-6-phosphate dehydrogenase and 10 mM MgCl2 in 100 mM K+ phosphate, pH 8.0. The drug inhibitors, quinidine, chlorpheniramine, yohimbine, imipramine, amjaline, propanolol, doxorubicin, haloperidol and corynanthine were diluted from stock solutions of 10 mM in acetonitrile to 120 µM in 100 mM K+ phosphate. Six consecutive 1:3 dilutions were made and 50 µl of each was added to appropriate wells on the assay plate. The CYP2D6 was diluted to a solution of 2 pmol/10 µl in 100 mM K+ phosphate and 10 µL was added to each well. 20 µl of buffer was added to each well containing standard. The drug inhibitors were allowed to pre-incubated with the CYP 2D6 enzyme for 1 hr prior to the addition of the MOBFC substrate. The MOBFC substrate was diluted to 26.6 µM (6.7× final assay concentration) in 100 mM K+ phosphate buffer, and 15 µl was added to appropriate wells on the plate. Data for a product fluorescence standard calibration curve was generated in the following manner. Hydroxy-trifluoro-methylcoumarin was diluted to 100 µM in K+ phosphate buffer, and seven consecutive 1:2 dilutions were made. 10 µl of each dilution was added to the appropriate wells on the plate containing 90 µl of 100 mM K+ phosphate, pH 8.0. After addition of 10 µL of 13 mM NADP+ solutions to all wells the assay plate was placed into the fluorescence microtiter plate reader and fluorescence measured at 3 minute intervals for 60 minutes. For MOBFC, the excitation filter was 395/25 nm and the emission filter was 530/25 nm. $IC_{50}$ values (value for 50% inhibition of fluorgenic substrate turnover) were determined and converted to apparent $k_i$ values according to the general method described in Henderson, P. J. F., *Statistical Analysis of Enzyme Kinetic Data,* "Enzyme Assays," Oxford University Press, 277–313 (1993).

TABLE 10

| DRUG | Apparent Ki values [uM] |
| --- | --- |
| Quinidine | 0.15 |
| Chlorpheniramine | 2.5 |
| Yohimbine | 10 |
| Imipramine | 0.1 |
| Amjaline | >30 |
| Propanolol | >30 |
| Doxorubicin | 8 |
| Haloperidol | 3 |
| Corynanthine | >30 |

Apparent $k_i$ values for inhibition of CYP 2D6 by drugs known to interact with the enzyme determined from $IC_{50}$ values of inhibition of MOBFC metabolism by the enzyme.

EXAMPLE 20

Preparation of 7-Benzyloxymethyloxycoumarin-3-carboxylic Acid Succinimidyl Ester 7-Benzyloxymethyloxycoumarin-3-carboxylic acid succinimidyl ester was prepared by following procedure: A mixture of 7-Hydroxycoumarin-3-carboxylic acid succinimidyl ester, (303 mg, 1 mmol) and dry potassium carbonate (248 mg, 1.5 mmol), in dry dimethylformamide (15 mL) was vigorously stirred at 0° C. for 25 min. Benzylchloromethylether (2.32 mL, 10.0 mmol), was then added quickly to the reaction. The bright yellow mixture was stirred at 0° C. for 45 min. and for 2 hrs. at 25° C. After which time the reaction turned to a colorless solution. The reaction was monitored by TLC ($R_f$=0.5, 1:1 EtOAc:Hex.and $R_f$=0.24, $CHCl_3$).

After of the coumarin starting material the reaction medium was diluted with diethylether (100 mL) and extracted with 50 mL of 5% aqueous acetic acid. The ether layer was separated and dried over anhydrous sodium sulfate, filtered and the solvents evaporated under reduced pressure. The solid was recrystallized from methanol and washed with hexanes (20 mL, 0° C.). The product, -Benzyloxymethyloxycoumarin-3-carboxylic acid succinimidyl ester, was dried under reduced pressure yielding a white solid (85 mg, 20%). $^1$H NMR (500 MHz, $CDCl_3$): δ 2.91 (s, 4H), 4.74 (s, 2H), 5.40 (s, 2H), 7.07 (m, 2H), 7.32 (m, 5H), 7.53 (d, 1H), 8.75 (s, 1H).

EXAMPLE 21

Coupling of 7-benzyloxymethyloxycoumarin-3-carboxylic Acid Succinimidyl Ester with Racemic 1,2 Diaminocyclohexanes) to Give the Product Designated BOM-09B Five (5) µmoles benzyloxymethyloxycoumarin-3-carboxylic acid succinimidyl ester in dry dimethylformamide (50 µL) were mixed with a 1 M solution a racemic mixture of 1,2 diaminocyclohexanes (50 µmoles) in a plastic centrifuge tube. The reaction was allowed to proceed with sonication at room temperature for 2 hrs, after which time 500 µL of deionized water was added to the tube and a white precipitate formed. The reaction was then spun down in a centrifuge and the solvent decanted. Results from UV-Vis spectra (absorbance maximum at 340 nm) and electrospray MS (M+H=423, M+Na=445) performed on a sample of the solid were consistent with the following product structure (mixture of stereo isomers):

BOM-O9B

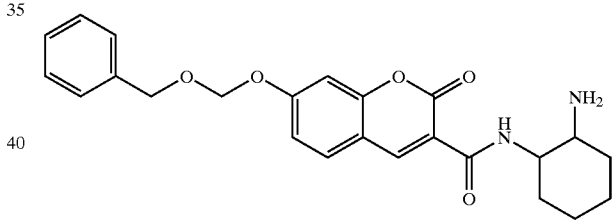

EXAMPLE 22

Determination of the Rate of Hydroxylation of BOM-09B by CYP 3A4

The racemic compound mixture (designated BOM-09B) was tested for activity with cytochrome P450 isozymes. BOM-09B showed particularly high activity with the CYP 3A4 isozyme. The CYP 3A4 assay was performed in a 96-well plate at 37° C. in a volume of 100 µL/well. BOM-09B was diluted from a stock solution of 1 mM in acetonitrile to a 4× concentration of 80 µM in 100 mM K+ phosphate buffer of which 25 µl was added to the appropriate wells. Enzyme buffer was prepared and 65 µl was added to each well on the plate, for final assay concentrations of 1.3 mM NADP+, 3.3 mM glucose-6-phosphate, 0.4 units/ml glucose-6-phosphate dehydrogenase and 10 mM $MgCl_2$ in 100 mM K+ phosphate, pH 8.0. The cytochrome P450 isozyme CYP3A4 was diluted to give a 2 pmol enzyme per well. Enzymic conversion of the substrate to products was allowed to proceed for 1 hour with fluorescence reads taken every 4 minutes on a fluorescence microtiter plate reader. The solution was illuminated with an 395/25 nm excitation filter and fluorescence emission was detected through a 460/40 nm the emission filter. The rate of conversion of this substrate (BOM-09B) was compared with the substrate BOMCC under identical conditions and found to be half that of BOMCC (conversion rate$_{(BOM-09B)}$=0.75 pmol substrate/pmol enzyme min).

large molar excess, the reactions with diamines result in positively charged candidate substrates, which are screened for activity against the CYP 2D6 isozyme, which are known to prefer positively charged substrates.

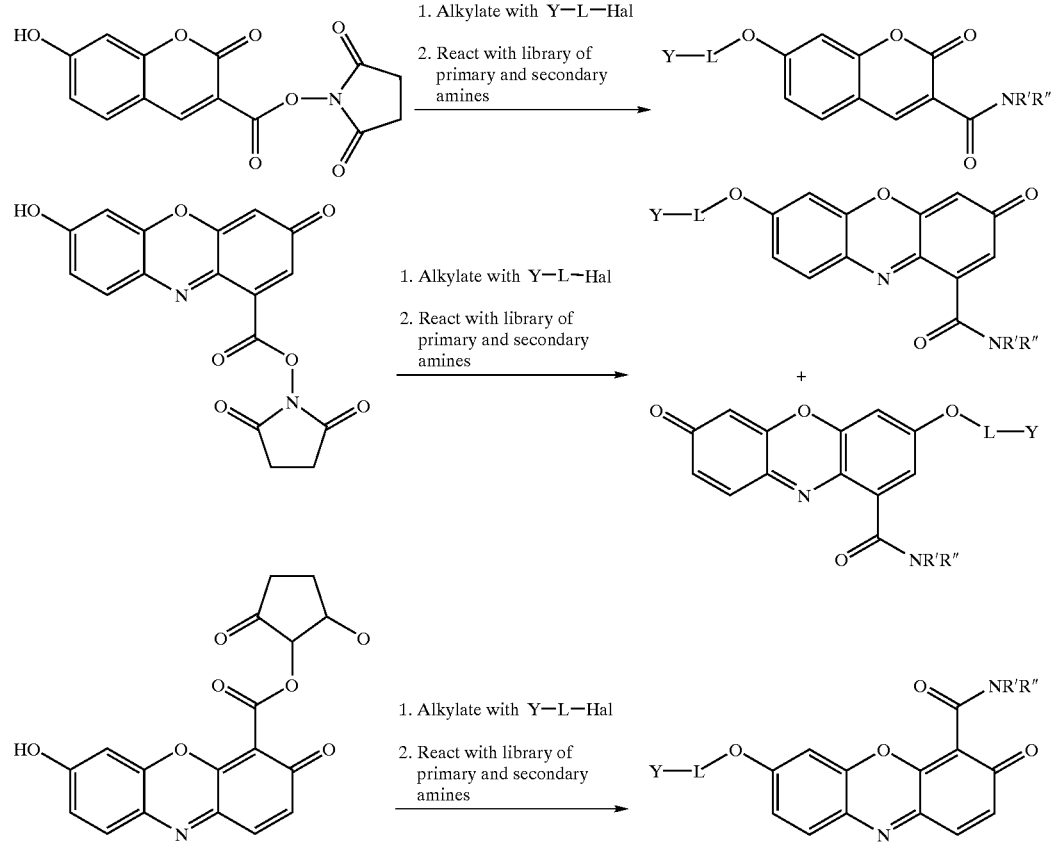

EXAMPLE 23

Synthesis of Fluorogenic Substrate Libraries from Highly Fluorescent Phenolic Dyes Libraries of ethers of 7-hydroxycoumarins and resorufin derivatives are synthesized as outlined below, i.e., the reaction paths leading to libraries of fluorogenic CYP450 candidate substrates are shown below. 7-Hydroxycoumarin-3-carboxylic acid succinimidyl ester is commercially available from Molecular Probes. The resorufin starting materials are readily prepared by following the procedures of U.S. Pat. Nos. 4,954,630 and 5,304,645, which describe the preparation of the acids and their conversion to the active esters using TSTU. The active esters of the dyes are stable to alkylation conditions needed to prepare ethers of the dye phenols. After alkylation the resulting fluorogenic dye ethers are modified at the active ester moiety by reaction with a library of primary and secondary aliphatic amines. The aliphatic sidechains are chosen to include diverse aromatic and heterocyclic moieties. 20 diamines are also included in the amine library. When reacted with the active dye esters in Compounds are purified by column chromatography or recrystallization after the alkylation of the dye phenol. Coupling with the amines is performed on a 10 μmol scale in dimethylformamide and usually proceeds in high yield. The reactions are followed in parallel by thin layer chromatography to ensure completion of the reactions and to detect and remove poorly reacting library members. The solvent is removed in high vacuum and excess amine removed by suspending the residue in 10% aqueous acetic acid, followed by recovery of the product by centrifugation. This procedure leads to compounds with sufficient purity (tested by TLC) for initial testing for metabolism by CYP450 enzymes. Promising substrates are resynthesized on a larger scale (100 μmol), purified by chromatography including separation of regio-isomers (resorufin-based substrates) and analyzed by electro-spray MS and analyzed by $^1$H-NMR.

EXAMPLE 24

Testing Libraries of Fluorogenic Substrates Against a Set of Human CYP450 Isozymes The libraries of newly synthesized putative substrates are dissolved at 2 mM concentration in appropriate water miscible organic solvents, with acetonitrile generally preferred, because up to 2% is generally tolerated by CYP450 enzymes. The different ether derivatives of any phenolic dye have similar extinction coefficients, allowing for calibration of the substrate concentration by absorbance. The solutions are transferred to 96 well storage plates to allow multiple automated parallel dispensation into 96 well microtitre assay plates. For rapid testing, all assays are performed in microtitre plates, using a Fluorstar or Cytofluor fluorescence plate reader to obtain the enzyme rates.

Initial experiments determine the conditions for each CYP450 isozyme (using commercially available human CYP450 isozymes expressed in insect microsomes from GENTEST) giving linear rates of product formation; the rate is proportional to the concentration of enzyme. The CYP450 isozymes tested to find more active substrates are: CYP 3A4, CYP 2D6, CYP 2C9, CYP 2C19. Testing also includes the CYP450 isozymes CYP 1A2, CYP 2E1, CYP 2B6, and CYP 2A6. This is to assess whether any substrate that is active with one of the isozymes 3A4, 2D6, or 2C9 and 2C19 is selective for that isozyme. Each isozyme requires slightly different conditions, and optimized variables include pH, NADPH concentration, concentration of CYP450, whether it is necessary to add cytochrome b as a cofactor, time of incubation, and effect of temperature, and other variables that will be apparent to those of skill in the art. In the initial screen for substrates, coumarin-based candidates are tested at 5 and 20 $\mu$M concentrations, resorufin-based candidates at 2 and 10 $\mu$M. The choice of different concentrations for ethers of resorufins versus ethers of coumarins takes into account the lower aqueous solubility of resorufin derivatives compared to coumarin derivatives and our finding in preliminary experiments that resorufin derivatives, being more hydrophobic, tend to bind more avidly to CYP450 enzymes (lower $K_m$). One pmol insect-expressed enzyme coexpressed with NADPH-cytochrome P450 reductase per well are used. The assay buffer will contain 10 mM $Mg^{2+}$ and the appropriate ionic strength of the assay solution is adjusted with from concentrated buffer stock solutions. NADPH needed for NADPH-cytochrome P450 reductase is supplied in the form of 1.3 mM $NADP^+$, which is converted to steady levels of NADPH by added glucose-6-phosphate dehydrogenase and 3 mM glucose-6-phosphate in the assay buffer. Apparent $k_{cat}$ and $K_m$ values for all active candidates are determined from eight-point dilutions of each substrate in duplicate, using the results from the preliminary tests to determine the actual concentration range for the accurate kinetic evaluation.

Optimization of assay conditions is accomplished through statistically validated Design of Experiments methodologies, using the commercial software package "Design-Expert®" produced by Stat-Ease® Inc. The data shown in FIGS. 4 and 5 were obtained with initial optimization.

EXAMPLE 25

Directed Synthesis of Fluorogenic Substrate Sets

Substrates found in the initial round of synthesis and testing are resynthesized on a larger scale (100 $\mu$mol) and purified by chromatography and/or recrystallization. Resorufin regio-isomeric ethers obtained in the synthesis are separated and kinetic properties determined for each separate isomer, as described above. Kinetic data obtained for these substrates will be used to direct the synthesis of a few small focused libraries. Additional alkyl halides and amines, closely related to the ones that result in activity with the isozyme, are purchased or synthesized with the goal of obtaining substrates with even higher activity and substrates that may be isozyme specific. The same synthetic routes as discussed in EXAMPLE 23. are followed, except that all compounds are purified and analyzed by NMR and MS before performing enzyme kinetics. These substrate candidates are tested in duplicate in eight-point dilutions using the results from the structurally-related substrates to determine the actual concentration range for the accurate kinetic evaluation.

EXAMPLE 26

Validation of Isozyme-Specific Substrates Using Human Liver Microsomes

Because human liver microsomes contain a range of CYP450 isozymes, only substrates that are specific for one of the insect-expressed human CYP450 enzymes are tested on commercially available human liver microsomal preparations. This verifies that, as generally expected, the specificity seen with the insect microsomal CYP450s is maintained in human liver microsomes. Initially, conditions for the assays are those specified by the suppliers of the microsomes. However, because the new substrates may have different kinetics to those for which the published conditions were designed, some optimization as described in EXAMPLE 24 is performed. All assays are carried out in 96 or 384-well microtitre plates as in EXAMPLE 24.

Specificity for one isozyme in the human liver microsomal preparations is confirmed by a lack of metabolism of the substrate in the presence of a selective CYP450 isozyme inhibitor for the isozyme being investigated. For example, inhibitors selective for CYP 3A4, CYP 2D6, and CYP 2C9 are troleandomycin, quinidine, and sulfaphenazole respectively. In addition, the fluorogenic substrate are used to determine $IC_{50}$ values for a panel of known CYP450 isozyme inhibitors, and the data compared to published values. For this step, an 8-point concentration curve of the inhibitors is performed in duplicate. Some difficulty may be encountered in that the published literature contains a large range of $IC_{50}$ values for any given inhibitor, often because of different experimental conditions between studies. Our results will be compared with the more relevant published studies, which have the most similar assay conditions.

EXAMPLE 27

Validate Screens Against Known CYP450 Inhibitors and Substrates

The most relevant CYP450 isozymes (CYP3A4, CYP2D6, CYP2C9, CYP2C19) are screened with their most appropriate novel fluorogenic substrates against a library of compounds containing known CYP 450 inhibitors. For this EXAMPLE, GENTEST recombinant human CYP450 isozymes expressed in insect microsomes are used. The library to be tested is the generic pharmacophore library from Microsource®, which has 480 biologically active molecules, including known CYP450 inhibitors and substrates.

Since the ultimate commercial value of the new CYP450 substrates is realized if the assays are adapted to high throughput, automated screening protocols, it is necessary to verify that the assay conditions developed in EXAMPLE 24 are suitable for automated use, and if not, to modify them appropriately. This is common practice with any assay which is to be run on a robotic system, and involves checking such parameters as: enzyme and substrate stability to allow a large number of assays to be run without constant manual intervention; reproducibility of the assay with the automated liquid handling systems; specific incubation times and temperatures suitable for the robotic scheduler; appropriate data capture and reduction routines, and other like parameters. It is also determined whether a "pre-read" of the plates prior to adding the NADPH to initiate the reaction will be necessary, since this can sometimes eliminate false positives caused by fluorescent compounds in the library.

Initially all compounds are tested at 10 μM concentration using the optimized robotic conditions, to determine in a simple hit/miss mode which compounds are interacting with which CYP450 isozyme. Although this involves testing four enzymes against 480 compounds (approx. 2,000 assays with controls), this only requires 25 96-well or 6 384-well microtitre plates, which can be run in a single day using currently available automated formats.

All hits are retested at 1 and 10 μM, and tested at 10 μM using a redox-sensitive red fluorescent dye identified to be suitable for checking that a compound is not interfering with the cytochrome P450 reductase step. $IC_{50}$ values are determined (using an eight-point curve in duplicate) for the known inhibitors or substrates and compare the data to published values. For the new substrates to be deemed suitable for routine high throughput screening of compounds as part of the drug development process, the assays must detect 100% of compounds with affinities for the relevant CYP450 isozyme of <1 μM, and >90% of compounds with affinities between 1 and 10 μM.

EXAMPLE 28

Determination of Whether a Test Compound is a Substrate for a CYP450 Isozyme

To determine whether a test compound is a substrate for a CYP450 isozyme the following experiment is conducted. A preparation of human CYP450 isozyme is treated with test compound for an incubation period of several hours under conditions suitable for metabolism of the test compound by the CYP450 isozyme. The residual CYP450 isozyme activity is assayed with a fluorogenic substrate for that CYP450 isozyme. The CYP450 isozyme is also treated with the same test compound for the same period of time but in the absence of NADP+, a condition that does not allow test compound metabolism. Following the incubation period, NADP+ is added, and the residual CYP450 isozyme activity is assayed with a fluorogenic substrate for that CYP450 isozyme. A CYP450 isozyme activity assayed under conditions suitable for metabolism of the test compound that is higher than the activity of the enzyme under conditions that do not allow test compound metabolism during the incubation period indicates that the test compound is a substrate of the CYP450 isozyme.

The assay is performed in a 96-well plate at room temperature and at a volume of 100 μl/well. 4× enzyme buffer is prepared and 25 μl is added to each well on the plate, for final assay concentrations of 3.3 mM glucose-6-phosphate, 0.4 units/ml glucose-6-phosphate dehydrogenase and 10 mM $MgCl_2$ in a K+ phosphate buffer of suitable concentration and at pH 8.0. The test compound is dissolved to 20 μM concentration in water and 50 μL of the solution is added to two wells each, followed by addition of 10 μL of buffer containing 10 pmol of the CYP450 isozyme. One of the two wells now receives 10 μL of 13 mM NADP+ and the test compound in both wells is incubated with the CYP450 isozyme for 2 hrs. Following incubation, the other well receives 10 μL of 13 mM NADP+ and both receive fluorogenic substrate, suitable for detection of activity of the CYP450 isozyme, in a 5 μL volume of buffer. The microtiter assay plate is transferred into the fluorescence microtiter plate reader and well fluorescence is measured at 3-minute intervals for 60 minutes. The rate in increase of well fluorescence is used to assess residual CYP450 isozyme activity in the wells. A result in which the residual CYP450 activity in the well that receives NADP+ prior to the incubation with the test compound is higher than in the duplicate well to which NADP+ is added after the incubation period indicates that the test compound is a substrate for the CYP450 isozyme.

The various articles of the scientific and/or medical literature, and the U.S. and foreign patents and patent applications cited herein are hereby incorporated by reference; each constitutes a part of the disclosure of this specification. Furthermore, while specific embodiments, working examples, and prophetic examples of the invention have been described in detail to illustrate the broad applicability and principles underlying the invention, it will be understood by those of skill in the art that the invention may be embodied otherwise without departing from such broad applicability and principles.

What is claimed is:

1. A kit for screening a candidate compound for activity as a substrate of at least one CYP450 enzyme, comprising:
   (a) an amount of a CYP450 enzyme, and
   (b) a reagent compound having the structure Y-L-Q, wherein:
   Y is selected from the group consisting of Q, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl and substituted heteroaryl; wherein if Y is selected from Q, L is L', wherein L' is selected from the group of —($CR^4H$)(—$OCR^2H$)$_p$, wherein each $R^2$ and each $R^4$ is separately selected from the group consisting of a hydrogen atom, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl and substituted heteroaryl and p is a positive integer no greater than twelve;
   L has the chemical structure L' or (—$OCR^2H$)$_p$—, wherein each $R^2$ is separately selected from the group consisting of a hydrogen atom, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl, substituted heteroaryl, and p is a positive integer no greater than twelve; and
   Q is a chemical means for generating an altered optical signal via cleavage of a C—O bond;
   wherein the amount of the CYP450 enzyme in the well is sufficient to produce a detectable optical signal upon interaction with a portion of the reagent compound.

2. The kit of claim 1, further comprising a container for containing at least a portion of the CYP450 enzyme and at least a portion of the reagent compound.

3. The kit of claim 1, further comprising a plate for containing at least a portion of the CYP450 enzyme and at least a portion of the reagent compound.

4. The kit of claim 1, further comprising a multi-well plate, in which each well is designed to contain at least a portion of the CYP450 enzyme and at least a portion of the reagent compound.

5. A kit for screening a candidate compound for CYP450 inhibitory activity, comprising:

(a) an amount of a CYP450 enzyme, and (b) a reagent compound having the structure Y-L-Q, wherein:

Y is selected from the group consisting of Q, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl and substituted heteroaryl; wherein if Y is selected from Q, L is L', wherein L' is selected from the group of —(CR$^4$H)(—OCR$^2$H)$_p$, wherein each R$^2$ and each R$^4$ is separately selected from the group consisting of a hydrogen atom, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl and substituted heteroaryl and p is a positive integer no greater than twelve;

L has the chemical structure L' or (—OCR$^2$H)$_p$—, wherein each R$^2$ is separately selected from the group consisting of a hydrogen atom, saturated $C_1$–$C_{20}$ alkyl, unsaturated $C_1$–$C_{20}$ alkenyl, unsaturated $C_1$–$C_{20}$ alkynyl, substituted saturated $C_1$–$C_{20}$ alkyl, substituted unsaturated $C_1$–$C_{20}$ alkenyl, substituted unsaturated $C_1$–$C_{20}$ alkynyl, $C_1$–$C_{20}$ cycloalkyl, $C_1$–$C_{20}$ cycloalkenyl, substituted saturated $C_1$–$C_{20}$ cycloalkyl, substituted unsaturated $C_1$–$C_{20}$ cycloalkenyl, aryl, substituted aryl, heteroaryl, substituted heteroaryl, and p is a positive integer no greater than twelve; and Q is a chemical means for generating an altered optical signal via cleavage of a C—O bond;

wherein the amount of the CYP450 enzyme in the well is sufficient to produce a detectable optical signal upon interaction with a portion of the reagent compound.

6. The kit of claim 5, further comprising a container for containing at least a portion of the CYP450 enzyme and at least a portion of the reagent compound.

7. The kit of claim 5, further comprising a plate for containing at least a portion of the CYP450 enzyme and at least a portion of the reagent compound.

8. The kit of claim 5, further comprising a multi-well plate, in which each well is designed to contain at least a portion of the CYP450 enzyme and at least a portion of the reagent compound.

9. The kit of claim 1, wherein the reagent compound is at least one of the following compounds: BOMR, BOMFC, BOMCC, EOMR, EOMCC, MOMCC, MOMFC, OOMR, BOM-DDAO, OOMCC, MOMR, and BOM-09B.

10. The kit of claim 5, wherein the reagent compound is at least one of the following compounds: BOMR, BOMFC, BOMCC, EOMR, EOMCC, MOMCC, MOMFC, OOMR, BOM-DDAO, OOMCC, MOMR, and BOM-09B.

* * * * *

UNITED STATES PATENT AND TRADEMARK OFFICE
CERTIFICATE OF CORRECTION

PATENT NO.     : 6,638,713 B2
DATED          : October 28, 2003
INVENTOR(S)    : Lewis R. Makings and Gregor Zlokarnik It is certified that error appears in the above-identified patent and that said Letters Patent is hereby corrected as shown below:

<u>Title page,</u>
Item [56], References Cited, OTHER PUBLICATIONS, first "Burke et al." reference, please delete "15-14" and insert -- 15-24 -- therefor; "Koller et al." reference, please delete "Monashefte" and insert -- Monatsheft -- therefor.

Signed and Sealed this

Eleventh Day of January, 2005

JON W. DUDAS
*Director of the United States Patent and Trademark Office*